US010894073B2

(12) United States Patent
Arvik et al.

(10) Patent No.: US 10,894,073 B2
(45) Date of Patent: Jan. 19, 2021

(54) PINOT NOIR GRAPE PRODUCTS FOR NONALCOHOLIC FATTY LIVER DISEASE AND OTHER USES

(71) Applicants: SONOMACEUTICALS, LLC, Santa Rosa, CA (US); THE UNITED STATES OF AMERICA, AS REPRESENTED BY THE SECRETARY OF AGRICULTURE, Washington, DC (US)

(72) Inventors: Torey James Arvik, Santa Rosa, CA (US); Hyunsook Kim, Seoul (KR); Wallace H. Yokoyama, Albany, CA (US); Scott R. Forsberg, Santa Rosa, CA (US)

(73) Assignees: SONOMACEUTICALS, LLC, Santa Rosa, CA (US); THE UNITED STATES OF AMERICA, AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 0 days.

(21) Appl. No.: 16/159,922

(22) Filed: Oct. 15, 2018

(65) Prior Publication Data
US 2019/0111099 A1 Apr. 18, 2019

Related U.S. Application Data

(63) Continuation of application No. 15/537,661, filed as application No. PCT/US2015/066585 on Dec. 18, 2015, now Pat. No. 10,130,671.

(60) Provisional application No. 62/094,963, filed on Dec. 20, 2014.

(51) Int. Cl.
| A61K 36/87 | (2006.01) |
| A61K 36/79 | (2006.01) |
| A61K 36/9066 | (2006.01) |
| A61K 36/28 | (2006.01) |
| A61K 45/06 | (2006.01) |

(52) U.S. Cl.
CPC .............. *A61K 36/87* (2013.01); *A61K 36/28* (2013.01); *A61K 36/79* (2013.01); *A61K 36/9066* (2013.01); *A61K 45/06* (2013.01)

(58) Field of Classification Search
None
See application file for complete search history.

(56) References Cited

U.S. PATENT DOCUMENTS

| 10,105,409 B2* | 10/2018 | Arvik | ............... A61P 3/10 |
| 2010/0173024 A1 | 7/2010 | McDaniel | |
| 2010/0255092 A1 | 10/2010 | Ravishankar et al. | |
| 2012/0269912 A1 | 10/2012 | Roberts | |
| 2015/0132419 A1 | 5/2015 | Arvik et al. | |
| 2015/0258032 A1 | 9/2015 | Lightburn | |
| 2019/0269748 A1* | 9/2019 | Arvik | ............... A61K 36/87 |

FOREIGN PATENT DOCUMENTS

| WO | 1999001148 A1 | 1/1999 |
| WO | 2013165921 A2 | 11/2013 |

OTHER PUBLICATIONS

Khoshbaten, M. et al. Grape Seed Extract to Improve Liver Function in Patients with Nonalcoholic Fatty Liver Change. The Saudi J of Gastroenterology 16(3)194-197, Jul./Sep. 2010. (Year: 2010).*
Yogalakshmi B. et al. Grape Seed Proanthocyanidin Rescues Rats from Steatosis. J of Lipids vol. 2013, pp. 1-11, 2013. (Year: 2013).*
Nonfinal Office Action dated Feb. 2, 2018 in U.S. Appl. No. 15/537,661.
Kim, H. et al. "Dietary Supplementation of Chardonnay Grape Seed Flour Reduces Plasma Cholesterol Concentration, Hepatic Steatosis, and Abdominal Fat Content in High-Fat Diet-Induced Obese Hamsters", J of Agric. Food Chem, 2014, 62:1919-1925.
Kang, J. et al., "A Combination of Grape Extract, Green Tea Extract, and L-Carnitine Improves High Fat Diet Induced Obesity,Hyperlipidemia and Non-alcoholic Fatty Liver Disease in Mice", Phytother Res. 2011 25 (12) 1789-1795.
Parry, J. et al., "Chemical Compositions, Antioxidant Capacities, and Antiproliferative Activities of Selected Fruit Seed Flours", 2006, J Agric Food Chem, 54:3773-3778.
Xu, Y. et al., "Freeze Dried Grape Powder Attenutates Mitochondria and Oxidative Stress Mediated Apoptosis in Liver Cells", J Agric Food Chem 2009, 57(19)9324-9331.
Park H. et al., "Modulation of Lipid Metabolism by Polyphenol Rich Grape Skin Extract Improves Liver Steatosis and Adiposity in High Fat Fed Mice", Mol. Nut. Food Res. 2013, 57(2) 360-364.
Rodrigo R. et al., "Dimunition of Tissue Lipid Peroxidation in Rats is Related to the In vitro Antioxidant Capacity of Wine", Life Sciences 2005, 76(8)889-900.
Rotches-Ribalta M. et al., "Pharmacokinetics of Resveratrol Metabolic Profile in Healthy Humans After Moderate Consumption of Red Wine and Grape Extract Tablets", Pharmacological Research, 2012 66(5) 375-382.
Pan M. et al., "Chemoprevention of Nonalcoholic Fatty Liver Disease by Dietary Natural Compounds", Mol. Nutr. Food Res. 2013, 58(1) 147-171.
Kim, Y. et al., "Polymeric Procyanidin Fraction from Defatted Grape Seeds Protects HepG2 Cells against Oxidative Stress by Inducing Phase II Enzymes via Nrf2 Activation", Food Sci. Biotechnol. 2013, 22(2)485-491.
Buchner I. et al., "Hepatoprotective and Antioxidant Potential of Organic and Conventional Grape Juices in Rats Fed a High-Fat Diet", 2014, 3(2) 323-338.
Dunn et al., "Modest alcohol consumption is associated with decreased prevalence of steatohepalitis in patients with non-alcoholic fatty liver disease (NAFLD)", J. Hepatol. (2012) vol. 57, No. 2, p. 384-92.

(Continued)

*Primary Examiner* — Ralph J Gitomer
(74) *Attorney, Agent, or Firm* — Troutman Pepper Hamilton Sanders LLP

(57) ABSTRACT

Embodiments described herein provide for uses of grape products, such as Chardonnay and Pinot Noir grape products and grape seed flour, for use in promoting a healthy liver, promoting healthy fat content in a liver, for treating or preventing NAFLD, and other embodiments and uses as described herein.

7 Claims, 3 Drawing Sheets

(56) References Cited

OTHER PUBLICATIONS

Notice of Allowance dated Jul. 5, 2018 in U.S. Appl. No. 15/537,661.
Khoshbaten et al., "Grape Seed Extract to Improve Liver Function in Patients with Nonalchohlic Fatty Liver Change", (2010) Saudi Journal of Gastroenterology, vol. 16, No. 3, 194-197.
Zhang et al., "Effect of Dietary Grape Pomace on Lipid Metabolism and Hepatic Morphology in Rats Fed a High Fat Diet", (2010) Korean Society of Food Science and Nutrition, vol. 39, No. 11, 1595-1603.
Hamlaoui-Gasmi et al., "Grape seed and skin extract mitigates garlic-induced oxidative stress in rat liver", (2012) Can. J. Physiol. Pharmacol., vol. 90, 547-556.
Charradi et al., "Protectiive effect of grape seed and skin extract against high-fat diet-induced liver steatosis and zinc depletion in rat, Digestive Diseases and Sciences", (2014) Vo 59, No. 8, p. 1768-1778.
Choi et al., "Suppression of oxidative stress by grape seed supplementation in rats", Nutr Res Pract (2012) 6(1):3-8.
Hwang Ik et al., Effects of grape seed extract and its ethylacetate / ethanol fraction on blood glucose levels in a model of type 2 diabetes, Phytotherapy Research, 2009, vol. 23, No. 8, p. 1182-1185.

\* cited by examiner

PINOT NOIR GRAPE PRODUCTS FOR NONALCOHOLIC FATTY LIVER DISEASE AND OTHER USES

CROSS-REFERENCE TO RELATED APPLICATIONS

The present application is a continuation of U.S. application Ser. No. 15/537,661, filed Jun. 19, 2017, now issued as U.S. Pat. No. 10,130,671, which is a National Stage Entry of International Application No. PCT/US2015/066586, filed Dec. 18, 2015, which claims priority to U.S. Provisional Patent Application No. 62/094,963, filed Dec. 20, 2014, which are incorporated by reference herein in their entirety.

FIELD

Embodiments described herein provide for uses of grape products, including, but not limited to Chardonnay grape products.

BACKGROUND

Nonalcoholic fatty liver disease (NAFLD) is recognized as a significant public health problem. Prevalence of NAFLD is 20% to 30% of the general population of Western countries. NAFLD ranges from steatosis (simple fatty liver) to nonalcoholic steatohepatitis (NASH), a condition that increases liver-related morbidity and mortality. Excessive hepatic lipid accumulation, oxidative and endoplasmic reticulum (ER) stress, and insulin resistance are the major manifestations of the progression of this disease. Without being bound to any particular theory, NAFLD can be caused, for example, by excessive hepatic lipid accumulation followed by increased oxidative stress and inflammation results in liver damage. NAFLD is a continuing problem. Embodiments described herein provide for solutions to these problems and others.

SUMMARY

Embodiments disclosed herein provide methods of treating or preventing non-alcoholic fatty liver disease (NAFLD) in a mammal comprising administering to the mammal an amount of a grape seed product effective to treat or prevent NAFLD.

Embodiments disclosed herein provide methods of reducing hepatic steatosis in a mammal comprising administering to the mammal an amount of a grape product effective to reduce hepatic steatosis.

Embodiments disclosed herein provide methods of reducing steatohepatitis in a mammal comprising administering to the mammal an amount of a grape product effective to reduce steatohepatitis.

Embodiments disclosed herein provide methods of reducing hepatic fibrosis in a mammal comprising administering to the mammal an amount of a grape product effective to reduce hepatic fibrosis.

Embodiments disclosed herein provide methods of treating or preventing non-alcoholic steatohepatitis (NASH) in a mammal comprising administering to the mammal an amount of a grape product effective to treat or prevent NASH.

Embodiments disclosed herein provide methods of supporting a healthy liver in a mammal comprising administering to the mammal an amount of a grape product effective to support a healthy liver.

In some embodiments of the methods described herein, the mammal has been identified as having non-alcoholic fatty liver disease. In some embodiments, the grape product reduces the amount of fat deposited in the liver.

Embodiments described herein provide pharmaceutical compositions comprising a grape product and at least one additional compound.

Embodiments disclosed herein provide methods of modulating the expression of one or more of the genes as described herein comprising administering a grape product to a mammal expressing one or more of the genes.

In some embodiments, the grape product is a grape seed flour, whole pomace or a fraction thereof (e.g., fractions of seed, skin, leaf, stem, and the like), grape extract (e.g. seed extract, skin extract, and the like), grape skin product (e.g., skin flower, skin powder, and the like), or any combination thereof, or any extract thereof. In some embodiments, the grape product is a Chardonnay product, such as, but not limited to a Chardonnay grape seed flour.

BRIEF DESCRIPTION OF FIGURES

FIG. 2A: Glucose tolerance in obese mice fed a high-fat (HF) diet supplemented with either 5% microcrystalline cellulose (MCC, control) or 10% (w/w) Chardonnay grape seed flour (ChrSd) for 5 weeks. (A) Glucose tolerance tests (GTT) were performed in the fasting state. FIG. 2B: Area under the curve (AUC) values (derived from FIG. 2A). Data are expressed as mean±SE. n=8-9/group. P<0.05.

FIG. 3A: Insulin tolerance in obese mice fed a high-fat (HF) diet supplemented with either 5% microcrystalline cellulose (MCC, control) or 10% (w/w) Chardonnay grape seed flour (ChrSd) for 5 weeks. (A) Insulin tolerance tests (ITTs) were performed in the fasting state. FIG. 3B: Area under the curve (AUC) values (derived from FIG. 3A). Data are expressed as mean±SE. n=8-9/group. P<0.05.

DETAILED DESCRIPTION

Figure 1:
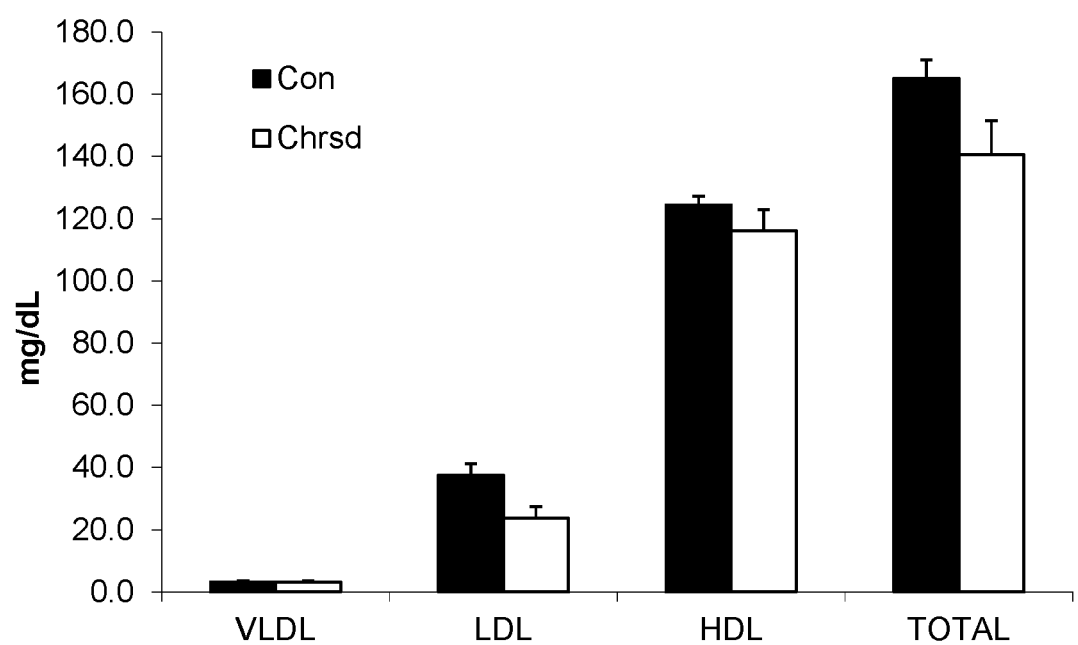
FIG. 1. Effect of Chardonnay grape seed flour (ChrSd) on plasma lipids. Male diet-induced obese mice (DIO) were fed high-fat (HF) diets containing 5% microcrystalline cellulose (MCC, control) or 10% (w/w) ChrSd for 5 weeks, and blood was collected in a food-deprived state. VLDL, very low-density lipoprotein; LDL, low-density lipoprotein; HDL, high-density lipoprotein. Data are expressed as means±SE; n=8-10/group. P<0.05.

Unless otherwise defined, all technical and scientific terms used herein have the same meaning as commonly understood by one of ordinary skill in the art. Although methods and materials similar or equivalent to those described herein can be used in the practice or testing, suitable methods and materials are described herein. All publications, patent applications, patents, and other references mentioned herein are incorporated by reference in their entirety. In the case of conflict, the present specification, including definitions, will control. In addition, the materials, methods, and examples are illustrative only and not intended to be limiting. Other features and advantages of the embodiments disclosed herein will be apparent from the present detailed description and claims.

The term "salt" or "salts" may refer to any acid addition salts, including addition salts of free acids or addition salts of free bases. All of these salts (or other similar salts) may be prepared by conventional means. All such salts are acceptable provided that they are non-toxic and do not substantially interfere with the desired pharmacological activity.

The terms "pharmaceutically acceptable" and/or "therapeutically acceptable" refer to molecular entities and compositions that are physiologically tolerable and preferably do not typically produce an allergic or similar untoward reaction, such as gastric upset, dizziness and the like, when administered to a human. In some embodiments, as used herein, the term "pharmaceutically acceptable" means approved by a regulatory agency of the Federal or a State government or listed in the U.S. Pharmacopeia or other generally recognized pharmacopeia (e.g., Remington's Pharmaceutical Sciences, Mack Publishing Co. (A. R. Gennaro edit. 1985)) for use in animals, and more particularly in humans.

The term "about" or "approximately" means plus or minus 5%.

As used herein and in the appended claims, the singular forms "a", "an", and "the" include plural reference unless the context clearly dictates otherwise.

As used herein the terms "comprise," "have," and "include" and their conjugates, as used herein, mean "including but not limited to." While various compositions, methods, and devices are described in terms of "comprising" various components or steps (interpreted as meaning "including, but not limited to"), the compositions, methods, and devices can also "consist essentially of" or "consist of" the various components and steps.

As used herein, the phrase "in need thereof" means that the animal or mammal has been identified or suspected as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent.

As used herein, the term "subject," "individual" or "patient," used interchangeably, means any animal, including mammals, such as mice, rats, other rodents, rabbits, dogs, cats, swine, cattle, sheep, horses, or primates, such as humans.

As used herein, the term "animal" includes, but is not limited to, humans and non-human vertebrates such as wild, domestic, and farm animals.

As used herein, the phrase "integer from X to Y" means any integer that includes the endpoints. That is, where a range is disclosed, each integer in the range including the endpoints is disclosed. For example, the phrase "integer from 1 to 5" discloses 1, 2, 3, 4, or 5 as well as the range 1 to 5.

As used herein, the term "mammal" means a rodent (i.e., a mouse, a rat, or a guinea pig), a monkey, a cat, a dog, a cow, a horse, a pig, or a human. In some embodiments, the mammal is a human.

As used herein, the terms "treat," "treated," or "treating" can refer to therapeutic treatment and/or prophylactic or preventative measures wherein the object is to prevent or slow down (lessen) an undesired physiological condition, disorder or disease, or obtain beneficial or desired clinical results. For purposes of the embodiments described herein, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment can also include eliciting a clinically significant response without excessive levels of side effects. Treatment also includes prolonging survival as compared to expected survival if not receiving treatment.

As described herein, grape products, such as Chardonnay grape products, may be used as a treatment for non-alcoholic fatty liver disease (NAFLD) and its more severe form, non-alcoholic steatohepatitis (NASH) in humans. Other embodiments are described herein.

Embodiments described herein relate to uses of grape products. In some embodiments, the grape product is a Chardonnay grape product. Other grape products are also described herein.

In some embodiments, grape product is a grape seed product. In some embodiments, the seed products contain the defatted portion of seed (e.g. grape seed), such as pomace meal, pomace flour, seed meal, or, in some embodiments, seed flour. In some embodiments, the seed product includes the contents of defatted seeds that are not extractable by an organic solvent, e.g., are not extractable by ethanol and/or methanol. In some embodiments, the seed product is prepared from seeds having an epicatechin content of at least 600 mg of epicatechin per 100 g of seeds or an epicatechin content of at least 700 mg of epicatechin per 100 g of seeds. In some embodiments, the epicatechin content ranges from 600-800 mg/100 g of seeds or from 650-800 mg/100 g of seeds.

As described herein, the grape product can be whole pomace or a portion thereof, grape skin product, grape seed product, or any combination thereof, or any extract thereof. Each of the products or extracts thereof can be used alone or in any combination with one another. The products or extracts can be derived from Chardonnay grapes, Cabernet Sauvignon grapes, Pinot Noir grape products, Sauvignon Blanc grape products, White Riesling grape products, and the like, or any combination thereof. In some embodiments, the grape is a grape grown in a coastal region. In some embodiments, the grape is a grape grown in a Winkler region climate type I, II, III, IV or V.

For the avoidance of doubt, a grape product is not a whole intact grape, but rather is a grape that has been processed. Examples of grape products are described herein.

As used herein, "seed meal" is ground whole seeds and "seed flour" is ground seed after the oil has been extracted. Seed flour may be obtained using the "cold press", "hot press" and solvent extraction processes as are known in the art to extract the oil from seeds yielding defatted seed flour. The meal or flour can be dried to the desired moisture content using conventional drying techniques suitable for drying food products.

The dried meal or flour can be further ground under ambient temperature conditions to form seed powder having free-flowing particles. In some embodiments, the free-flowing particles can range from a size not exceeding 841 microns (20 mesh) to a size not exceeding 37 microns (400 mesh). In certain embodiments, the size does not exceed 20 mesh, 40 mesh, 60 mesh, 80 mesh, 100 mesh, 200 mesh, 300 mesh, or 400 mesh.

In some embodiments, seed flour is made by separating and drying grape seeds, for example from the pomace produced after grapes are pressed to produce grape juice (e.g., to make wine). The grape seeds can be "cold-pressed"

to defat them (producing seed oil as a byproduct). Grape seed flours are milled from the press cake after the oil is expelled. In one embodiment, after juicing the grape the seed is separated from the skins, cleaned, mechanically defatted, finely milled and sifted to create an 100-80 mesh (149-177 micron) flowable powder.

Seed flour can also be purchased from a variety of sources. For example, certain types of grape seed flour can be purchased from Après Vin (Yakima, Wash.), Botanical Oil Innovations (Spooner, Wis.) or Fruitsmart, Inc. (Grandview, Wash.). The seed flour can sometimes be purchased as an 80 mesh flowable powder. In some embodiments, this is product is further milled and sifted to produce a flour with a smaller particle size.

In some embodiments, skins, stems and leaves (the remainder of pomace) are removed from the seeds prior to pressing. Removal of the skins, stems, and leaves allows for optimal oil pressing.

In some embodiments, the grape product is whole grape pomace or a portion thereof including fractions of seed, skin, leaf, stem, and the like. These fractions can also be present in a mixture of different ratios.

"Seed extract" can be made by solvent extraction of grape seeds with a suitable solvent, such as ethanol or methanol. For example, a grape seed extract, such as, but not limited to Chardonnay seed extract, can be made using a 40% ethanol solution as the extraction solvent. The extraction process, in addition to the extract containing the solvent soluble components, also produces a residue of non-soluble solids. The seed extract can then be combined with other grape products described herein or be used alone. Other extracts of the pomace can also be used. Extracts of skins can also be used or prepared.

In addition to the grape seed products disclosed herein other grape products can also be used in the methods. The other grape seed products can be used in the place of, or in combination with, the Chardonnay seed products. Examples of other grape seed products include, but are not limited to, Syrah grape seed products, Cabernet Sauvignon grape seed products, Pinot Noir grape seed products, Sauvignon Blanc grape seed products, White Riesling grape seed products, and the like.

The seed products can be included in a variety of food products, such as nutritional beverages (e.g., nutritional shakes), baked goods (e.g., cookies, brownies, cake, breads, biscuits, crackers), puddings, confections (i.e., candy), snack foods (e.g., pretzels), ice cream, frozen confections and novelties, or non-baked, extruded food products such as bars, including health or energy bars. The Chardonnay seed product can also be provided as a nutritional supplement, either in tablet or capsule form, or as a powder for use as a nutritional food or beverage additive.

In some embodiments, the seed product can be blended with other dry food materials for use in the preparation of food products enriched with seed products. Dry food materials include, for example, dry starch-containing materials, dry protein-containing materials or combinations thereof. Suitable starch-containing materials may be derived from, for example, rice, corn, soybeans, hemp, sunflower, canola, wheat, oats, rye, potato, or any combination thereof. Suitable dry protein-containing materials may be derived from for example, meat, milk, fish or any combination thereof. For baking applications, the seed product is suitable used in an amount ranging from 3% to 15% of the dry food material (e.g., white or whole wheat flour). The dry food may optionally also include additional ingredients such as vitamins, mineral fortifiers, salts, colors, flavors, flavor enhancers or sweeteners.

Seed products can be incorporated into beverages, processed meats, frozen desserts, confectionery products, dairy-type products, sauce compositions, and cereal grain products. Beverage products include, for example, smoothies, infant formula, fruit juice beverages, yogurt beverages, coffee beverages, beers, dry beverage mixes, tea fusion beverages, sports beverages, soy liquors, casca seca, soda, slushes, and frozen beverage mixes. Meat products include, for example, ground chicken products, water-added ham products, bologna, hot dogs, franks, chicken patties, chicken nuggets, beef patties, fish patties, surimi, bacon, luncheon meat, sandwich fillings, deli meats, meat snacks, meatballs, jerky, fajitas, bacon bits, injected meats, and bratwurst. Confectionery products include, for example, chocolates, mousses, chocolate coatings, yogurt coatings, cocoa, frostings, candies, energy bars, and candy bars. Frozen dessert products include, for example, ice cream, malts, shakes, popsicles, sorbets, and frozen pudding products. Dairy-type products include, for example, yogurt, cheese, ice cream, whipped topping, coffee creamer, cream cheese, sour cream, cottage cheese, butter, mayonnaise, milk-based sauces, milk-based salad dressings, and cheese curds. Cereal grain products include, for example, breads, muffins, bagels, pastries, noodles, cookies, pancakes, waffles, biscuits, semolina, chips, tortillas, cakes, crackers, breakfast cereals (including both ready-to-eat and cooked cereals), pretzels, dry bakery mixes, melba toast, breadsticks, croutons, stuffing, energy bars, doughnuts, cakes, popcorn, taco shells, fry coatings, batters, breading, crusts, brownies, pies, puffed soy cakes, crepes, croissants, flour, and polenta. Sauce compositions include salad dressings, nut butter spreads (e.g., peanut butter spreads), marinades, sauces, salsas, jams, cheese sauces, mayonnaise, tartar sauce, soy humus, dips, fruit syrups, and maple syrups. Sauce composition may also include a suspending agent to aid in maintaining the uniformity of the composition. Examples of suitable suspending agents include polysaccharides, such as starch, cellulose (e.g., microcrystalline cellulose) and carrageenan, and polyuronides, such as pectin. Gelatin is another example of a suspending agent which may be used in the beverage compositions as well. Examples of additional supplemented food products prepared using the premixes described herein include, but are not limited to, tofu, formulated soy essence, powdered protein supplements, juice mixable protein supplements, foaming agents, clouding agents, baby foods, meatless balls, meat analogues, egg products (e.g., scrambled eggs), soups, chowders, broth, milk alternatives, soy-milk products, chili, spice mixes, sprinkles, soy whiz, salad topping, edible films, edible sticks, chewing gum, bacon bits, veggie bits, pizza crust barriers, soy pie, no-gas synthetic beans, soy helper, soy cotton candy, fruit bits, pizza rolls, mashed potatoes, spun soy protein fiber, soy roll-ups, extruded snacks, condiments, lotions, fries, gelatin dessert products, vitamin supplements, nutritional bars, dry cake, bread or muffin mixes, and microwavable instant dry mixes.

In some embodiments, the seed product may be provided as an energy bar (suitable for consumption during physical activity) or a meal replacement bar. The energy bar or meal replacement bar can also contain one or more vitamin, mineral, food supplement, botanical, or plant or herb extracts or ingredients known in the art or used in energy bars or meal replacement bars, such as a fruit juice or extract, an herb or herb flavor, natural or artificial flavors, vitamins, minerals, anti-oxidant containing extracts, coenzyme Q, omega-3 fatty acids, guarana, caffeine, theobromine, maltodextrin, and protein. In some embodiments, the energy bar or meal replacement bar can have total available energy levels of carbohydrates/protein/fat of 40/30/30 respectively.

The energy and meal replacement bars can be further supplemented for athletic performance enhancement, mental energy or cognitive focus enhancement, and/or nutritional benefit. Exemplary supplements include, but are not limited to Vinpocetine, Vincamine Ginkgo *Biloba*, L-Arginine, Acetyl-L-Carnitine, Feverfew, DMAE (Dimethylaminoethanol), DMAE bitartrate, P-chlorophenoxyacetate, Vitamin B-Complex, *Ginseng,* 5 HTP (5-Hydroxytryptophan), L-Theanine, Androstenedione, L-Glutamine, L-Tyrosine, L-Glycine, L-lysine, Whey Protein, and DHEA (Dehydroepiandrosterone), or any combination thereof.

The seed product or composition can also contain an amount of one or more additional grape seeds or grape skin products which is/are not the first seed product. In some embodiments, an amount of the first seed product is replaced in the seed composition with an amount of the second grape seed or grape skin product. The amount of second grape seed or grape skin product that will need to be added to the seed composition to attain the same benefit as a given amount of seed product can readily be determined by those skilled in the art.

The seed products prepared according to the methods described herein can also be used, for example, in pharmaceutical compositions and formulations. The pharmaceutical compositions can be formulated by standard techniques using one or more physiologically acceptable carriers or excipients. In some embodiments, the formulations may contain a buffer and/or a preservative. The compounds and their physiologically acceptable salts and solvates can be formulated for administration by any suitable route, including via inhalation, topically, nasally, orally, parenterally (e.g., intravenously, intraperitoneally, intravesically or intrathecally) or rectally in a vehicle comprising one or more pharmaceutically acceptable carriers, the proportion of which is determined by the solubility and chemical nature of the peptide, chosen route of administration and standard biological practice.

According to some embodiments, pharmaceutical compositions are provided comprising effective amounts of one or more compound(s) made according to the methods described herein together with, for example, pharmaceutically acceptable diluents, preservatives, solubilizers, emulsifiers, adjuvants and/or other carriers. Such compositions include diluents of various buffer content (e.g., TRIS or other amines, carbonates, phosphates, amino acids, for example, glycinamide hydrochloride (especially in the physiological pH range), N-glycylglycine, sodium or potassium phosphate (dibasic, tribasic), etc. or TRIS-HCl or acetate), pH and ionic strength; additives such as detergents and solubilizing agents (e.g., surfactants such as Pluronics, Tween 20, Tween 80 (Polysorbate 80), Cremophor, polyols such as polyethylene glycol, propylene glycol, etc.), antioxidants (e.g., ascorbic acid, sodium metabisulfite), preservatives (e.g., Thimersol, benzyl alcohol, parabens, etc.) and bulking substances (e.g., sugars such as sucrose, lactose, mannitol, polymers such as polyvinylpyrrolidones or dextran, etc.); and/or incorporation of the material into particulate preparations of polymeric compounds such as polylactic acid, polyglycolic acid, etc. or into liposomes. Hyaluronic acid may also be used. Such compositions can be employed to influence the physical state, stability, rate of in vivo release, and rate of in vivo clearance of a compound of the present invention. See, e.g., Remington's Pharmaceutical Sciences, 18th Ed. (1990, Mack Publishing Co., Easton, Pa. 18042) pages 1435-1712 which are herein incorporated by reference. The compositions can, for example, be prepared in liquid form, or can be in dried powder, such as lyophilized form. Particular methods of administering such compositions are described infra. The compositions can also be crystallized or precipitated. Examples of methods of crystallizing or precipitating can be found, for example, in U.S. Provisional Application No. 61/936,914, filed Feb. 7, 2014, which is hereby incorporated by reference in its entirety.

Where a buffer is to be included in the formulations, the buffer can be selected from the group consisting of sodium acetate, sodium carbonate, citrate, glycylglycine, histidine, glycine, lysine, arginin, sodium dihydrogen phosphate, disodium hydrogen phosphate, sodium phosphate, and tris(hydroxymethyl)-aminomethan, or mixtures thereof. Each one of these specific buffers constitutes an alternative embodiment. In some embodiments the buffer is glycylglycine, sodium dihydrogen phosphate, disodium hydrogen phosphate, sodium phosphate or mixtures thereof.

Where a pharmaceutically acceptable preservative is to be included in the formulations of the invention, the preservative is selected from the group consisting of phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof. Each one of these specific preservatives constitutes an alternative embodiment. In some embodiments, the preservative is phenol or m-cresol.

In some embodiments, the preservative is present in a concentration from about 0.1 mg/ml to about 50 mg/ml, in a concentration from about 0.1 mg/ml to about 25 mg/ml, or in a concentration from about 0.1 mg/ml to about 10 mg/ml. In some embodiments, the preservative is present in a concentration from about 1 mg/ml to about 50 mg/ml, in a concentration from about 1 mg/ml to about 25 mg/ml, or in a concentration from about 1 mg/ml to about 10 mg/ml.

The use of a preservative in pharmaceutical compositions is well-known to the skilled person. For convenience reference is made to Remington: The Science and Practice of Pharmacy, 19th edition, 1995.

In some embodiments, the formulation may further comprise a chelating agent where the chelating agent may be selected from salts of ethylenediaminetetraacetic acid (EDTA), citric acid, and aspartic acid, and mixtures thereof. Each one of these specific chelating agents constitutes an alternative embodiment.

In some embodiments, the chelating agent is present in a concentration from 0.1 mg/ml to 5 mg/ml, from 0.1 mg/ml to 2 mg/ml, or from 2 mg/ml to 5 mg/ml.

The use of a chelating agent in pharmaceutical compositions is well-known to the skilled person. For convenience reference is made to Remington: The Science and Practice of Pharmacy, 19th edition, 1995.

In some embodiments, the formulation may further comprise a stabilizer selected from the group of high molecular weight polymers or low molecular compounds where such stabilizers include, but are not limited to, polyethylene glycol (e.g. PEG 3350), polyvinylalcohol (PVA), polyvinylpyrrolidone, carboxymethylcellulose, different salts (e.g. sodium chloride), L-glycine, L-histidine, imidazole, arginine, lysine, isoleucine, aspartic acid, tryptophan, threonine and mixtures thereof. Each one of these specific stabilizers constitutes an alternative embodiment. In some embodiments, the stabilizer is selected from the group consisting of L-histidine, imidazole and arginine.

In some embodiments, the high molecular weight polymer is present in a concentration from 0.1 mg/ml to 50 mg/ml, from 0.1 mg/ml to 5 mg/ml, from 5 mg/ml to 10 mg/ml, from 10 mg/ml to 20 mg/ml, from 20 mg/ml to 30 mg/ml or from 30 mg/ml to 50 mg/ml.

In some embodiments, the low molecular weight compound is present in a concentration from 0.1 mg/ml to 50 mg/ml, from 0.1 mg/ml to 5 mg/ml, from 5 mg/ml to 10 mg/ml, from 10 mg/ml to 20 mg/ml, from 20 mg/ml to 30 mg/ml, or from 30 mg/ml to 50 mg/ml.

The use of a stabilizer in pharmaceutical compositions is well-known to the skilled person. For convenience reference is made to Remington: The Science and Practice of Pharmacy, 19th edition, 1995.

In some embodiments, the formulation may further comprise a surfactant where a surfactant may be selected from a detergent, ethoxylated castor oil, polyglycolyzed glycerides, acetylated monoglycerides, sorbitan fatty acid esters, poloxamers, such as 188 and 407, polyoxyethylene sorbitan fatty acid esters, polyoxyethylene derivatives such as alkylated and alkoxylated derivatives (tweens, e.g. Tween-20, or Tween-80), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, kephalins, phosphatidyl serine), glyceroglycolipids (galactopyransoide), sphingophospholipids (sphingomyelin), and sphingoglycolipids (ceramides, gangliosides), DSS (docusate sodium, docusate calcium, docusate potassium, SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the postively charged DODAC, DOTMA, DCP, BISHOP, lysophosphatidylserine and lysophosphatidylthreonine, zwitterionic surfactants (e.g. N-alkyl-N,N-dimethylammonio-1-propanesulfonates, 3-cholamido-1-propyldimethylammonio-1-propanesulfonate, dodecylphosphocholine, myristoyl lysophosphatidylcholine, hen egg lysolecithin), cationic surfactants (quarternary ammonium bases) (e.g. cetyl-trimethylammonium bromide, cetylpyridinium chloride), non-ionic surfactants, polyethyleneoxide/polypropyleneoxide block copolymers (Pluronics/Tetronics, Triton X-100, Dodecyl β-D-glucopyranoside) or polymeric surfactants (Tween-40, Tween-80, Brij-35), fusidic acid derivatives—(e.g. sodium tauro-dihydrofusidate etc.), long-chain fatty acids and salts thereof C6-C12 (e.g. oleic acid and caprylic acid), acylcarnitines and derivatives, Nα-acylated derivatives of lysine, arginine or histidine, or side-chain acylated derivatives of lysine or arginine, Nα-acylated derivatives of dipeptides comprising any combination of lysine, arginine or histidine and a neutral or acidic amino acid, Nα-acylated derivative of a tripeptide comprising any combination of a neutral amino acid and two charged amino acids, or the surfactant may be selected from the group of imidazoline derivatives, or mixtures thereof. Each one of these specific surfactants constitutes an alternative embodiment.

The use of a surfactant in pharmaceutical compositions is well-known to the skilled person. For convenience reference is made to Remington: The Science and Practice of Pharmacy, 19th edition, 1995.

In some embodiments, the composition can comprises a sweetener, including pharmaceutically acceptable sweeteners. Examples of pharmaceutically acceptable sweeteners can include at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1', 6'-trideoxygalactosucrose). In some embodiments, it includes saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners can also be used, for example, in low concentrations. For example, in the case of sodium saccharin, the concentration may range from 0.04% to 0.1% (w/v) based on the total volume of the final formulation, and can be about 0.06% in the low-dosage formulations and about 0.08% in the high-dosage ones. The bulk sweetener can effectively be used in larger quantities ranging from about 10% to about 35% or from about 10% to 15% (w/v).

The formulations may be prepared by conventional techniques, e.g. as described in Remington's Pharmaceutical Sciences, 1985 or in Remington: The Science and Practice of Pharmacy, 19th edition, 1995, where such conventional techniques of the pharmaceutical industry involve dissolving and mixing the ingredients as appropriate to give the desired end product.

The compositions and products described herein can also be administered by any method known in the art. For example, administration may be transdermal, parenteral, intravenous, intra-arterial, subcutaneous, intramuscular, intracranial, intraorbital, ophthalmic, intraventricular, intracapsular, intraspinal, intracisternal, intraperitoneal, intracerebroventricular, intrathecal, intranasal, aerosol, by suppositories, or oral administration. In some embodiments, a pharmaceutical composition of the compounds prepared herein can be for administration for injection, or for oral, pulmonary, nasal, transdermal, ocular administration.

For oral administration, the composition can be formulated in unit dosage forms such as capsules or tablets. The tablets or capsules may be prepared by conventional methods with pharmaceutically acceptable excipients, including binding agents, for example, pregelatinised maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulphate. Tablets can be coated by methods well known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound. The compounds can also be prepared with cyclodextrins or other large molecules to facilitate oral adsorption.

For topical administration, the composition can be formulated in a pharmaceutically acceptable vehicle containing 0.1 to 10 percent or 0.5 to 5 percent of the active compound(s). Such formulations can be in the form of a cream, lotion, sublingual tablet, aerosols and/or emulsions and can be included in a transdermal or buccal patch of the matrix or reservoir type as are conventional in the art for this purpose.

For parenteral administration, the compositions can be administered by intravenous, subcutaneous, or intramuscular injection, in compositions with pharmaceutically acceptable vehicles or carriers. The compositions can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use.

For administration by injection, the compositions can be administered in solution in a sterile aqueous vehicle which may also contain other solutes such as buffers or preservatives as well as sufficient quantities of pharmaceutically acceptable salts or of glucose to make the solution isotonic. In some embodiments, the pharmaceutical compositions may be formulated with a pharmaceutically acceptable carrier to provide sterile solutions or suspensions for injectable administration. In particular, injectables can be prepared in conventional forms, either as liquid solutions or suspensions, solid forms suitable for solution or suspensions in liquid prior to injection or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized. Suitable pharmaceutical carriers are described in "Remington's pharmaceutical Sciences" by E. W. Martin.

For administration by inhalation, the compositions may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch. For intranasal administration the compositions of the invention may be used, for example, as a liquid spray, as a powder or in the form of drops.

The compositions can also be formulated in rectal compositions, for example, suppositories or retention enemas, for example, containing conventional suppository bases, for example, cocoa butter or other glycerides.

Furthermore, the compositions can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

The compositions prepared according to the methods described herein may be administered to a patient at effective doses, including therapeutically effective doses, to prevent, treat, or control diseases and disorders described herein. They can also be used to restore or maintain a healthy liver as described herein. Pharmaceutical compositions may be administered to a patient in an amount sufficient to elicit an effective maintenance, protective, restorative, or therapeutic response in the patient. An amount adequate to accomplish this is defined as "therapeutically effective dose." The dose will be determined by the efficacy of the particular composition employed and the condition of the subject, as well as the body weight or surface area of the area to be treated. The size of the dose also will be determined by the existence, nature, and extent of any adverse effects that accompany the administration of a particular compound or vector in a particular subject.

Toxicity and therapeutic efficacy of such compositions can be determined by standard pharmaceutical procedures in cell cultures or experimental animals, for example, by determining the LD50 (the dose lethal to 50% of the population) and the ED50 (the dose therapeutically effective in 50% of the population). The dose ratio between toxic and therapeutic effects is the therapeutic index and can be expressed as the ratio, LD50/ED50. Compositions that exhibit large therapeutic indices are preferred. While compositions that exhibit toxic side effects can be used, care should be taken to design a delivery system that targets such compounds to the site of affected tissue to minimize potential damage to normal cells and, thereby, reduce side effects.

The data obtained from cell culture assays and animal studies can be used to formulate a dosage range for use in humans. The dosage of such compounds lies preferably within a range of circulating concentrations that include the ED50 with little or no toxicity. The dosage can vary within this range depending upon the dosage form employed and the route of administration. For any composition used in the methods described herein, the therapeutically effective dose can be estimated initially, for example, from cell culture assays. A dose can be formulated in animal models to achieve a circulating plasma concentration range that includes the IC50 (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a modulator is from about 1 ng/kg to 10 mg/kg for a typical subject or as described elsewhere herein.

The amount and frequency of administration of the compositions will be regulated according to the judgment of the user or attending clinician considering such factors as age, condition and size of the patient as well as severity of the symptoms being treated. An ordinarily skilled physician or veterinarian can readily determine and prescribe the effective amount of the drug required to prevent, counter or arrest the progress of the condition. In general it is contemplated that an effective amount would be from 0.001 mg/kg to 10 mg/kg body weight, and in particular from 0.01 mg/kg to 1 mg/kg body weight or as otherwise described herein. In some embodiments, it is contemplated that an effective amount would be to continuously infuse by intravenous administration from 0.01 micrograms/kg body weight/min to 100 micrograms/kg body weight/min for a period of 12 hours to 14 days. It may be appropriate to administer the required dose as two, three, four or more sub-doses at appropriate intervals throughout the day. Said sub-doses may be formulated as unit dosage forms, for example, containing 0.01 to 500 mg, and in particular 0.1 mg to 200 mg of the composition per unit dosage form.

In some embodiments, the pharmaceutical preparation is in a unit dosage form. In such form, the preparation is subdivided into suitably sized unit doses containing appropriate quantities of the active component, e.g., an effective amount to achieve the desired purpose. The quantity of active compound in a unit dose of preparation may be varied or adjusted from about 0.01 mg to about 1000 mg, from about 0.01 mg to about 750 mg, from about 0.01 mg to about 500 mg, or from about 0.01 mg to about 250 mg, according to the particular application. The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

In some embodiment of the methods, the amount of grape product consumed as a percentage of daily diet is at least 3%, at least 5%, or at least 8% by mass. In some embodiments, 5-10%, 7%, or 10% of the daily diet by mass is consumed.

In some embodiments of the methods, the amount of grape product consumed as a percentage of daily diet is at least 3%, at least 5%, or at least 8% of total calories consumed. In some embodiments, 5-10%, 7%, or 10% of the daily calories are from the grape product.

In some embodiments of the methods, the grape product, whole pomace or any portion thereof, skin product, seed flour, or seed product, or any extract thereof, or any combination of the foregoing is administered in an amount from about 1 mg to about 15,000 mg, from about 1 mg to about 14,000 mg, about 1 mg to about 13,000 mg, about 1 mg to about 12,000 mg, about 1 mg to about 11,000 mg, about 1 mg to about 10,000 mg, about 1 mg to about 9,000 mg, about 1 mg to about 8,000 mg, about 1 mg to about 7,000 mg, about 1 mg to about 6,000 mg, about 1 mg to about 5,000 mg, about 1 mg to about 4,000 mg, about 1 mg to about 3,000 mg, about 1 mg to about 2,000 mg, about 1 mg to about 1,000 mg, about 1 mg to about 900 mg, about 1 mg to about 800 mg, about 1 mg to about 700 mg, about 1 mg to about 600 mg, about 1 mg to about 500 mg, about 1 mg to about 400 mg, about 1 mg to about 300 mg, about 1 mg to about 200 mg, about 1 mg to about 100 mg, about 1 mg to about 75 mg, about 1 mg to about 50 mg, or about 1 mg to about 25 mg.

In some embodiments of the methods, the grape product, whole pomace or any portion thereof, skin product, seed flour, or seed product, or any extract thereof, or any combination of the foregoing is administered in an amount from about 5 mg to about 15,000 mg, from about 5 mg to about 14,000 mg, about 5 mg to about 13,000 mg, about 5 mg to about 12,000 mg, about 5 mg to about 11,000 mg, about 5 mg to about 10,000 mg, about 5 mg to about 9,000 mg, about 5 mg to about 8,000 mg, about 5 mg to about 7,000 mg, about 5 mg to about 6,000 mg, about 5 mg to about 5,000 mg, about 5 mg to about 4,000 mg, about 5 mg to about 3,000 mg, about 5 mg to about 2,000 mg, about 5 mg to about 1,000 mg, about 5 mg to about 900 mg, about 5 mg to about 800 mg, about 5 mg to about 700 mg, about 5 mg to about 600 mg, about 5 mg to about 500 mg, about 5 mg to about 400 mg, about 5 mg to about 300 mg, about 5 mg to about 200 mg, about 5 mg to about 100 mg, about 5 mg to about 75 mg, about 5 mg to about 50 mg, or about 5 mg to about 25 mg.

In some embodiments of the methods, the grape product, whole pomace or any portion thereof, skin product, seed flour, or seed product, or any extract thereof, or any combination of the foregoing is administered in an amount from about 10 mg to about 15,000 mg, from about 10 mg to about 14,000 mg, about 10 mg to about 13,000 mg, about 10 mg to about 12,000 mg, about 10 mg to about 11,000 mg, about 10 mg to about 10,000 mg, about 10 mg to about 9,000 mg, about 10 mg to about 8,000 mg, about 10 mg to about 7,000 mg, about 10 mg to about 6,000 mg, about 10 mg to about 5,000 mg, about 10 mg to about 4,000 mg, about 10 mg to about 3,000 mg, about 10 mg to about 2,000 mg, about 10 mg to about 1,000 mg, about 10 mg to about 900 mg, about 10 mg to about 800 mg, about 10 mg to about 700 mg, about 10 mg to about 600 mg, about 10 mg to about 500 mg, about 10 mg to about 400 mg, about 10 mg to about 300 mg, about 10 mg to about 200 mg, about 10 mg to about 100 mg, about 10 mg to about 75 mg, about 10 mg to about 50 mg, or about 10 mg to about 25 mg.

In some embodiments of the methods, the grape product, whole pomace or any portion thereof, skin product, seed flour, or seed product, or any extract thereof, or any combination of the foregoing is administered in an amount from about 25 mg to about 15,000 mg, from about 25 mg to about 14,000 mg, about 25 mg to about 13,000 mg, about 25 mg to about 12,000 mg, about 25 mg to about 11,000 mg, about 25 mg to about 10,000 mg, about 25 mg to about 9,000 mg, about 25 mg to about 8,000 mg, about 25 mg to about 7,000 mg, about 25 mg to about 6,000 mg, about 25 mg to about 5,000 mg, about 25 mg to about 4,000 mg, about 25 mg to about 3,000 mg, about 25 mg to about 2,000 mg, about 25 mg to about 1,000 mg, about 25 mg to about 900 mg, about 25 mg to about 800 mg, about 25 mg to about 700 mg, about 25 mg to about 600 mg, about 25 mg to about 500 mg, about 25 mg to about 400 mg, about 25 mg to about 300 mg, about 25 mg to about 200 mg, about 25 mg to about 100 mg, about 25 mg to about 75 mg, or about 25 mg to about 50 mg.

In some embodiments of the methods, the grape product, whole pomace or any portion thereof, skin product, seed flour, or seed product, or any extract thereof, or any combination of the foregoing is administered in an amount from about 50 mg to about 15,000 mg, from about 50 mg to about 14,000 mg, about 50 mg to about 13,000 mg, about 50 mg to about 12,000 mg, about 50 mg to about 11,000 mg, about 50 mg to about 10,000 mg, about 50 mg to about 9,000 mg, about 50 mg to about 8,000 mg, about 50 mg to about 7,000 mg, about 50 mg to about 6,000 mg, about 50 mg to about 5,000 mg, about 50 mg to about 4,000 mg, about 50 mg to about 3,000 mg, about 50 mg to about 2,000 mg, about 50 mg to about 1,000 mg, about 50 mg to about 900 mg, about 50 mg to about 800 mg, about 50 mg to about 700 mg, about 50 mg to about 600 mg, about 50 mg to about 500 mg, about 50 mg to about 400 mg, about 50 mg to about 300 mg, about 50 mg to about 200 mg, about 50 mg to about 100 mg, or about 50 mg to about 75 mg.

In some embodiments of the methods, the grape product, whole pomace or any portion thereof, skin product, seed flour, or seed product, or any extract thereof, or any combination of the foregoing is administered in an amount from about 75 mg to about 15,000 mg, from about 75 mg to about 14,000 mg, about 75 mg to about 13,000 mg, about 75 mg to about 12,000 mg, about 75 mg to about 11,000 mg, about 75 mg to about 10,000 mg, about 75 mg to about 9,000 mg, about 75 mg to about 8,000 mg, about 75 mg to about 7,000 mg, about 75 mg to about 6,000 mg, about 75 mg to about 5,000 mg, about 75 mg to about 4,000 mg, about 75 mg to about 3,000 mg, about 75 mg to about 2,000 mg, about 75 mg to about 1,000 mg, about 75 mg to about 900 mg, about 75 mg to about 800 mg, about 75 mg to about 700 mg, about 75 mg to about 600 mg, about 75 mg to about 500 mg, about 75 mg to about 400 mg, about 75 mg to about 300 mg, about 75 mg to about 200 mg, or about 75 mg to about 100 mg.

In some embodiments of the methods, the grape product, whole pomace or any portion thereof, skin product, seed flour, or seed product, or any extract thereof, or any combination of the foregoing is administered in an amount from about 100 mg to about 15,000 mg, from about 100 mg to about 14,000 mg, about 100 mg to about 13,000 mg, about 100 mg to about 12,000 mg, about 100 mg to about 11,000 mg, about 100 mg to about 10,000 mg, about 100 mg to about 9,000 mg, about 100 mg to about 8,000 mg, about 100 mg to about 7,000 mg, about 100 mg to about 6,000 mg, about 100 mg to about 5,000 mg, about 100 mg to about 4,000 mg, about 100 mg to about 3,000 mg, about 100 mg to about 2,000 mg, about 100 mg to about 1,000 mg, about 100 mg to about 900 mg, about 100 mg to about 800 mg, about 100 mg to about 700 mg, about 100 mg to about 600 mg, about 100 mg to about 500 mg, about 100 mg to about 400 mg, about 100 mg to about 300 mg, or about 100 mg to about 200 mg.

In some embodiments of the methods, the grape product, whole pomace or any portion thereof, skin product, seed flour, or seed product, or any extract thereof, or any combination of the foregoing is administered in an amount from about 200 mg to about 15,000 mg, from about 200 mg to about 14,000 mg, about 200 mg to about 13,000 mg, about 200 mg to about 12,000 mg, about 200 mg to about 11,000 mg, about 200 mg to about 10,000 mg, about 200 mg to about 9,000 mg, about 200 mg to about 8,000 mg, about 200 mg to about 7,000 mg, about 200 mg to about 6,000 mg, about 200 mg to about 5,000 mg, about 200 mg to about 4,000 mg, about 200 mg to about 3,000 mg, about 200 mg to about 2,000 mg, about 200 mg to about 1,000 mg, about 200 mg to about 900 mg, about 200 mg to about 800 mg, about 200 mg to about 700 mg, about 200 mg to about 600 mg, about 200 mg to about 500 mg, about 200 mg to about 400 mg, or about 200 mg to about 300 mg.

In some embodiments of the methods, the grape product, whole pomace or any portion thereof, skin product, seed flour, or seed product, or any extract thereof, or any combination of the foregoing is administered in an amount from about 300 mg to about 15,000 mg, from about 300 mg to about 14,000 mg, about 300 mg to about 13,000 mg, about 300 mg to about 12,000 mg, about 300 mg to about 11,000 mg, about 300 mg to about 10,000 mg, about 300 mg to about 9,000 mg, about 300 mg to about 8,000 mg, about 300 mg to about 7,000 mg, about 300 mg to about 6,000 mg, about 300 mg to about 5,000 mg, about 300 mg to about 4,000 mg, about 300 mg to about 3,000 mg, about 300 mg to about 2,000 mg, about 300 mg to about 1,000 mg, about 300 mg to about 900 mg, about 300 mg to about 800 mg, about 300 mg to about 700 mg, about 300 mg to about 600 mg, about 300 mg to about 500 mg, or about 300 mg to about 400 mg.

In some embodiments of the methods, the grape product, whole pomace or any portion thereof, skin product, seed flour, or seed product, or any extract thereof, or any combination of the foregoing is administered in an amount from about 400 mg to about 15,000 mg, from about 400 mg to about 14,000 mg, about 400 mg to about 13,000 mg, about 400 mg to about 12,000 mg, about 400 mg to about 11,000 mg, about 400 mg to about 10,000 mg, about 400 mg to about 9,000 mg, about 400 mg to about 8,000 mg, about 400 mg to about 7,000 mg, about 400 mg to about 6,000 mg, about 400 mg to about 5,000 mg, about 400 mg to about 4,000 mg, about 400 mg to about 3,000 mg, about 400 mg to about 2,000 mg, about 400 mg to about 1,000 mg, about 400 mg to about 900 mg, about 400 mg to about 800 mg, about 400 mg to about 700 mg, about 400 mg to about 600 mg, about 400 mg to about 500 mg.

In some embodiments of the methods, the grape product, whole pomace or any portion thereof, skin product, seed flour, or seed product, or any extract thereof, or any combination of the foregoing is administered in an amount from about 500 mg to about 15,000 mg, from about 500 mg to about 14,000 mg, about 500 mg to about 13,000 mg, about 500 mg to about 12,000 mg, about 500 mg to about 11,000 mg, about 500 mg to about 10,000 mg, about 500 mg to about 9,000 mg, about 500 mg to about 8,000 mg, about 500 mg to about 7,000 mg, about 500 mg to about 6,000 mg, about 500 mg to about 5,000 mg, about 500 mg to about 4,000 mg, about 500 mg to about 3,000 mg, about 500 mg to about 2,000 mg, about 500 mg to about 1,000 mg, about 500 mg to about 900 mg, about 500 mg to about 800 mg, about 500 mg to about 700 mg, or about 500 mg to about 600 mg.

In some embodiments of the methods, the grape product, whole pomace or any portion thereof, skin product, seed flour, or seed product, or any extract thereof, or any combination of the foregoing is administered in an amount from about 600 mg to about 15,000 mg, from about 600 mg to about 14,000 mg, about 600 mg to about 13,000 mg, about 600 mg to about 12,000 mg, about 600 mg to about 11,000 mg, about 600 mg to about 10,000 mg, about 600 mg to about 9,000 mg, about 600 mg to about 8,000 mg, about 600 mg to about 7,000 mg, about 600 mg to about 6,000 mg, about 600 mg to about 5,000 mg, about 600 mg to about 4,000 mg, about 600 mg to about 3,000 mg, about 600 mg to about 2,000 mg, about 600 mg to about 1,000 mg, about 600 mg to about 900 mg, about 600 mg to about 800 mg, or about 600 mg to about 700 mg.

In some embodiments of the methods, the grape product, whole pomace or any portion thereof, skin product, seed flour, or seed product, or any extract thereof, or any combination of the foregoing is administered in an amount from about 700 mg to about 15,000 mg, from about 700 mg to about 14,000 mg, about 700 mg to about 13,000 mg, about 700 mg to about 12,000 mg, about 700 mg to about 11,000 mg, about 700 mg to about 10,000 mg, about 700 mg to about 9,000 mg, about 700 mg to about 8,000 mg, about 700 mg to about 7,000 mg, about 700 mg to about 6,000 mg, about 700 mg to about 5,000 mg, about 700 mg to about 4,000 mg, about 700 mg to about 3,000 mg, about 700 mg to about 2,000 mg, about 700 mg to about 1,000 mg, about 700 mg to about 900 mg, or about 700 mg to about 800 mg.

In some embodiments of the methods, the grape product, whole pomace or any portion thereof, skin product, seed flour, or seed product, or any extract thereof, or any combination of the foregoing is administered in an amount from about 800 mg to about 15,000 mg, from about 800 mg to about 14,000 mg, about 800 mg to about 13,000 mg, about 800 mg to about 12,000 mg, about 800 mg to about 11,000 mg, about 800 mg to about 10,000 mg, about 800 mg to about 9,000 mg, about 800 mg to about 8,000 mg, about 800 mg to about 7,000 mg, about 800 mg to about 6,000 mg, about 800 mg to about 5,000 mg, about 800 mg to about 4,000 mg, about 800 mg to about 3,000 mg, about 800 mg to about 2,000 mg, about 800 mg to about 1,000 mg, or about 800 mg to about 900 mg.

In some embodiments of the methods, the grape product, whole pomace or any portion thereof, skin product, seed flour, or seed product, or any extract thereof, or any combination of the foregoing is administered in an amount from about 900 mg to about 15,000 mg, from about 900 mg to about 14,000 mg, about 900 mg to about 13,000 mg, about 900 mg to about 12,000 mg, about 900 mg to about 11,000 mg, about 900 mg to about 10,000 mg, about 900 mg to about 9,000 mg, about 900 mg to about 8,000 mg, about 900 mg to about 7,000 mg, about 900 mg to about 6,000 mg, about 900 mg to about 5,000 mg, about 900 mg to about 4,000 mg, about 900 mg to about 3,000 mg, about 900 mg to about 2,000 mg, or about 900 mg to about 1,000 mg.

In some embodiments of the methods, the grape product, whole pomace or any portion thereof, skin product, seed flour, or seed product, or any extract thereof, or any combination of the foregoing is administered in an amount from about 1,000 mg to about 15,000 mg, from about 1,000 mg to about 14,000 mg, about 1,000 mg to about 13,000 mg, about 1,000 mg to about 12,000 mg, about 1,000 mg to about 11,000 mg, about 1,000 mg to about 10,000 mg, about 1,000 mg to about 9,000 mg, about 1,000 mg to about 8,000 mg, about 1,000 mg to about 7,000 mg, about 1,000 mg to about 6,000 mg, about 1,000 mg to about 5,000 mg, about 1,000 mg to about 4,000 mg, about 1,000 mg to about 3,000 mg, or about 1,000 mg to about 2,000 mg.

In some embodiments, the amount of grape product, whole pomace or any portion thereof, skin product, seed flour, or seed product, or any extract thereof, or any combination of the foregoing consumed daily is at least, or about 0.1 g, at least, or about, 0.5 g, is at least, or about, 1 g, is at least, or about, 2 g, is at least, or about, 3 g, is at least, or about, 4 g, is at least, or about 5 g, at least, or about, 10 g, at least, or about, 15 g, at least, or about, 20 g, at least, or about, 25 g, at least, or about, 30 g, at least, or about, 35 g, at least, or about, 40 g, or at least, or about, 45 g. In some embodiments, at least, or about, 50 g of the grape product is consumed daily.

In some embodiments, the amount of grape product, whole pomace or any portion thereof, skin product, seed flour, or seed product, or any extract thereof, or any combination of the foregoing consumed daily is at least 1 tablespoon, at least 2 tablespoons, at least 3 tablespoons, at least 4 tablespoons, or at least 5 tablespoons.

In some embodiments, the amount of grape product, whole pomace or any portion thereof, skin product, seed flour, or seed product, or any extract thereof, or any combination of the foregoing consumed daily on a weight:body weight basis is at least 0.2 g/kg, at least 0.5 g/kg, or at least 0.7 g/kg. In some embodiments, at least 1 g of the grape product per kg of body weight is consumed per day.

Seed flour can be substituted or combined with whole pomace or any portion thereof, pomace meal, pomace flour, skin flour, skin product, seed product, or seed meal, or any extract of the thereof, or any combination of the foregoing is administered in any of the methods or embodiments disclosed herein. The amount of pomace meal, pomace flour, skin flour, seed extract, or seed meal that will need to be consumed daily to attain the same benefit as a given amount of seed flour can readily be determined by those skilled in the art and as described herein. For example, it is expected that a subject will need to consume about three times as much skin flour to achieve the same benefit as a given amount of seed flour.

In some embodiments, the grape product is taken at least twice a week, at least 3 times a week, or every other day. In some embodiments, the grape product is incorporated into the daily diet. In some embodiments, the product is administered twice a day, three times a day, or four times a day.

The grape product can be taken for an amount of time sufficient to treat and/or prevent a condition amenable to treatment and/or prevention by seed product as described herein. The grape product can be taken for at least one week, at least 2 weeks, at least 3 weeks, at least one month, at least 2 months, at least 3 months, at least 6 months, at least a year, or indefinitely.

In some embodiments of the methods, a second grape product which is not the first grape product is administered to the individual. In some embodiments, the combination of the first grape product and second grape product (seed, skin, pomace, and the like) provides a therapeutic effect or health benefit which is greater than the effect of administration of first grape product alone.

In some embodiments, the amount of the first grape product and amount of the second grape product or grape seed, pomace, or skin product are selected so that the effect achieved is at least the same as the effect achieved by a given amount of the first seed product administered alone.

In some embodiments, methods of treating or preventing non-alcoholic fatty liver disease (NAFLD) in a mammal are provided. In some embodiments, the methods comprise administering to the mammal an amount of grape product effective to treat or prevent NAFLD. In some embodiments, the grape product is a grape seed product. In some embodiments, the grape product is a combination or extract of the different grape products described herein. In some embodiments, the seed product is Chardonnay seed product. Non-alcoholic fatty liver disease is a term used to describe the accumulation of fat in the liver of people who drink little or no alcohol. In some embodiments, mammal consumes no alcohol. In some embodiments, the mammal has inflammation of the liver. In some embodiments, the mammal has scarring in the liver. The form of NAFLD with the scarring can be referred to as nonalcoholic steatohepatitis. In some embodiments, the mammal with NAFLD can also have liver failure. The compositions described herein can be used to treat or ameliorate any of these conditions.

In some embodiments, methods of reducing hepatic steatosis in a mammal comprising administering to the mammal an amount of a grape product effective to reduce hepatic steatosis. In some embodiments, the grape product is a Chardonnay grape product.

In some embodiments, methods of reducing steatohepatitis in a mammal comprising administering to the mammal an amount of a grape product effective to reduce steatohepatitis are provided. In some embodiments, the grape product is a Chardonnay grape product. In some embodiments, the grape product is a grape seed product or extract thereof.

In some embodiments, methods of reducing hepatic fibrosis in a mammal are provided. In some embodiments, the methods comprise administering to the mammal an amount of a grape seed product effective to reduce hepatic fibrosis. In some embodiments, the grape product is a Chardonnay grape product. In some embodiments, the grape product is a grape seed product or extract thereof.

In some embodiments, methods of treating or preventing non-alcoholic steatohepatitis (NASH) in a mammal are provided. In some embodiments, the methods comprise administering to the mammal an amount of a grape product effective to treat or prevent NASH. In some embodiments, the grape product is a Chardonnay grape product. In some embodiments, the grape product is a grape seed product or extract thereof.

In some embodiments, methods of supporting a healthy liver in a mammal are provided. In some embodiments, the method comprises administering to the mammal an amount of a grape product effective to support a healthy liver. In some embodiments, the healthy liver is supported by preserving the normal function of the liver. This can be done, for example, by the enhancing or preserving the liver's ability to metabolize energy. In some embodiments, this is done by supporting the immune response to protect and/or support the liver from external insult.

In some embodiments, methods of controlling acute stress-induced damage to a liver in a subject due to exposure to environmental toxins and/or consumed products are provided. In some embodiments, the method comprises administering to the subject an amount of a grape product as described herein.

In some embodiments, methods of modulating miRNAs in a subject's liver that ameliorate the toxic stress response is provided. In some embodiments, the method comprises administering to the subject an amount of a grape product as described herein.

In some embodiments, methods of increasing the ability of a liver in a subject to regenerate and/or heal are provided. In some embodiments, the method comprises administering to the subject an amount of a grape product as described herein.

The grape products can also be used to inhibit or treat oxidative stress. The products can also be used to maintain a healthy oxidative stress level in the mammal. The methods comprise administering to the mammal an effective amount of a grape seed product described herein. In some embodiments, the oxidative stress is present in the liver. In some embodiments, the grape seed products can be used to reduce liver inflammation.

In some embodiments, methods of reducing or preventing oxidative stress in a mammal's liver are provided. In some embodiments, the methods comprise administering to the mammal an amount of a grape product effective to reduce or prevent oxidative stress in the mammal's liver. In some embodiments, the method reduces or prevents lipid peroxidation in the liver.

In some embodiments, methods of protecting, supporting, enhancing, or maintaining cytochrome P450 and/or Phase II enzymatic detoxification system in a mammal's liver are provided, wherein the methods comprise administering to the mammal an amount of a grape product effective to protect, support, enhance, or maintain cytochrome P450 and/or Phase II enzymatic detoxification system in the mammal's liver.

In some embodiments, methods of upregulating expression of genes that control production of detoxification enzymes in a mammal are provided, wherein the methods comprise administering to the mammal an amount of a grape product effective to upregulate expression of genes that control production of detoxification enzymes in the mammal. In some embodiments, the gene is NRF2.

In some embodiments, methods of increasing production of antioxidants in a mammal are provided, wherein the methods comprise administering to the mammal an amount of a grape product effective to increase the production of antioxidants in the mammal. In some embodiments, the antioxidant increased is glutathione, superoxide dismutase, or catalase.

In the various embodiments described herein, the mammal or subject can be a mammal or a subject in need thereof. In some embodiments, the mammal has been identified as having non-alcoholic fatty liver disease or related conditions, which are described herein. In some embodiments, the grape product reduces the amount of fat deposited in the liver in the mammal.

As described herein, the grape seed product can be a grape seed flour. Accordingly, in some embodiments, the seed flour can also be a Chardonnay seed flour. In some embodiments, the grape seed product is a grape seed extract. In some embodiments, the extract is a Chardonnay seed extract.

As described herein, the composition can contain a grape product and at least one additional compound. In some embodiments, the compound is an antioxidant. In some embodiments, the at least one additional compound is vitamin E, cinnamon, black bear bile, obeticholic acid, 2,4-dinitrophenol (DNP), DNP-methyl ether (DNPME), an anti-glycemic compound, or an anti-cholesterol compound. In some embodiments, the at least one additional compound is vitamin A, vitamin C, a carotenoid, lipoic acid, ubiquinol, ubiquinone, or glutathione. In some embodiments, the at least one additional compound is a second type of grape seed product. That is, the composition can comprise grape seed compositions derived from two or more different types of grapes. The types of grapes can be any type, such as those, but not limited to, the grapes described herein.

In some embodiments, the anti-glycemic compound is an insulin sensitizer. Examples of insulin sensitizers include, but are not limited to, pioglitazone, metformin, sulfonylureas, or thiazolidinediones.

In some embodiments, the anti-cholesterol compound is a HMG-CoA reductase inhibitor. These can sometimes be referred to colloquially as "statins." In some embodiments, the HMG-CoA reductase inhibitor is atorvastatin, fluvastatin, lovastatin, pitavastatin, pravastatin, rosuvastatin, or simvastatin.

In some embodiments, the method comprises administering the grape product and the additional product concurrently or in series. The products can, therefore, be administered sequentially or simultaneously. In some embodiments, the grape product and the at least one additional compound or composition are combined into the same formulation or unit dosage form and administered together. The unit dosage form, as described herein, can be, for example, a powder, capsule or tablet. In some embodiments, the different compositions are administered in separate formulations.

Formulations comprising a grape product and at least one additional compound or composition are also provided. In some embodiments, the at least one additional compound or composition is a second type of grape product. In some embodiments, the composition comprises a grape product and at least one additional compound. In some embodiments, it is an antioxidant. In some embodiments, the at least one additional compound is vitamin E, obeticholic acid, 2,4-dinitrophenol (DNP), DNP-methyl ether (DNPME), an anti-glycemic compound, or an anti-cholesterol compound. In some embodiments, the at least one additional compound is vitamin A, vitamin C, a carotenoid, lipoic acid, ubiquinol, ubiquinone, or glutathione. In some embodiments, the at least one additional compound is a methyl donor, such as, but not limited to, s-adenosyl-methionine, trimethyl glycine, or methionine. In some embodiments, the at least one additional compound is a metabolic nutrient, such as, but not limited to, a phosphatide, an essential fatty acid, choline, or a B vitamin. In some embodiments, the at least one additional compound is a botanical or a botanical extract, such as, but not limited to, milk thistle, schizandra, burdock dandelion, artichoke, turmeric, celandine, kudzu, chicory, or yellow dock, or any extract thereof. Examples of the anti-glycemic compound or an anti-cholesterol compound are described herein. For example, in some embodiments, the anti-glycemic compound is an insulin sensitizer. In some embodiments, the insulin sensitizer is pioglitazone, metformin, thiazolidinediones, or sulfonylureas. In some embodiments, the composition comprises an anti-cholesterol compound is a HMG-CoA reductase inhibitor. In some embodiments, the HMG-CoA reductase inhibitor is atorvastatin, fluvastatin, lovastatin, pitavastatin, pravastatin, rosuvastatin, or simvastatin.

In some embodiments, the composition is suitable for mammal (e.g. human, livestock, husbanded animal, pet) consumption. In some embodiments, the composition is suitable for cattle, poultry, dogs, cats, and the like. In some embodiments, the compositions described herein are combined with a probiotic. Therefore, in some embodiments, in the methods described herein, the subject is a mammal (e.g. human, livestock, husbanded animal, pet). In some embodiments, the subject is cattle, poultry, dogs, cats, and the like.

In some embodiments, the compositions described herein can be used to increase insulin resistance. In some embodiments, the compositions described herein can be used to maintain normal (e.g. healthy) insulin resistance. In some embodiments, the compositions described herein can be used to maintain a healthy level of hepatic leptin. In some embodiments, the compositions described herein can be used to restore hepatic leptin to healthy or normal levels. In some embodiments, the compositions described herein can be used to improve, maintain, or restore hepatic leptin sensitivity in a mammal, including a mammal in need thereof. Accordingly, the compositions can be used to reduce hepatic steatosis.

In some embodiments, the compositions can be used to reduce the liver and/or epididymal adipose tissue weights by 30-40% as compared to a mammal on a diet without the grape product (e.g. seed extract or flour). In some embodiments, the compositions are used to reduce the hepatic lipid content by about 40-50% in a mammal on a high fat diet as compared to a mammal on a control diet. In some embodiments, the compositions are used to reduce the hepatic lipid content in a mammal. The compositions can be administered according to the various methods described herein in, for example, an amount described herein.

Embodiments disclosed herein also provide methods of modulating the expression of one or more of the genes described herein. In some embodiments, the methods comprise administering a grape extract (e.g. seed extract, pomace, or flour) to a mammal expressing one or more of the genes. In some embodiments, methods of modulating the expression of a gene in a mammal comprising administering a grape seed extract to the mammal in an effective amount to modulate the expression of the gene are provided. In some embodiments the gene expression is increased. In some embodiments, the gene expression is decreased. In some embodiments, the mammal is a mammal in need of modulated gene expression. In some embodiments, the expression of the gene is increased or decreased at least 1.5 fold as compared to the mammal not administered the grape seed extract. In some embodiments, the expression of the gene is increased decreased at least 2, 3, 4, 5, or 6 fold. In some embodiments, the expression of the gene is increased or decreased about 1.5 to 6, 1.5 to 5, 1.5 to 4, 1.5 to 3, 1.5 to 2, 2 to 6, 2 to 5, 2 to 4, 2 to 3, 3 to 6, 3 to 5, 3 to 4, 4 to 6, 4 to 5, 5 to 6, or 6 to 7 fold. In some embodiments, the gene expression is modulated according to the amounts shown in the Examples.

In some embodiments, the gene is one or more of Chi3l1, Ces1d, Adra1b, Slc13a3, Ntrk2, Cyp21a1, Aqp8, Gck, Pfkm, Txn1, Ckb, Gckr, Fen1, Cyp46a1, Vldlr, Ppcdc, Bdh2, Scd1, Acot11, Mlxip1 (ChREBP), Lcn13, Prodh, Gstt3, Mc5r, Tas2r104, Vmn1r192, Ras12-9, Cfd, Ctse, Orm2, Rorc, Tlr5, Hnmt, Cyp2b13, Cyp2d40, Hao2, Gdf15, Sptlc3, Mogat1, Plin4, Ifna9, Asns, Got1, Atp6v0d2, Cyp7b1, Cyp17a1, Id1, Avpr1a, Ocln, Cyp51, Fdft1, Hmgcr, Hsd17b7, Insig1, Lss, Mvd, Mvk, Nsdhl, Sc4 mol, Tm7sf2, Apom, Lepr, Pcsk9, Sqle, Il17rb, Acs13, Agxt, Aldoc, Pgk2, Tlr13, Hmgcs1, Stard4, Mmp7, and Igfbp2. In some embodiments, the gene is 2, 3, 4, or 5 of the preceding list. In some embodiments, the gene is each of the genes of the preceding list.

Embodiments provided herein also include, but are not limited to:

1. A method of treating or preventing non-alcoholic fatty liver disease (NAFLD) in a mammal comprising administering to the mammal an amount of a grape product effective to treat or prevent NAFLD.
2. A method of reducing hepatic steatosis in a mammal comprising administering to the mammal an amount of a grape product effective to reduce hepatic steatosis.
3. A method of reducing steatohepatitis in a mammal comprising administering to the mammal an amount of a grape product effective to reduce steatohepatitis.
4. A method of reducing hepatic fibrosis in a mammal comprising administering to the mammal an amount of a grape product effective to reduce hepatic fibrosis.
5. A method of treating or preventing non-alcoholic steatohepatitis (NASH) in a mammal comprising administering to the mammal an amount of a grape product effective to treat or prevent NASH.
6. A method of supporting a healthy liver in a mammal comprising administering to the mammal an amount of a grape product effective to support a healthy liver.
7. The method of embodiment 6, wherein the mammal has been identified as having non-alcoholic fatty liver disease.
8. A method of reducing or preventing oxidative stress in a mammal's liver comprising administering to the mammal an amount of a grape product effective to reduce or prevent oxidative stress in the mammal's liver.
9. The method of embodiment 8, wherein the method reduces or prevents lipid peroxidation.

10. A method of protecting, supporting, enhancing, or maintaining cytochrome P450 and/or Phase II enzymatic detoxification system in a mammal's liver comprising administering to the mammal an amount of a grape product effective to protect, support, enhance, or maintain cytochrome P450 and/or Phase II enzymatic detoxification system in the mammal's liver.

11. A method of upregulating expression of genes that control production of detoxification enzymes in a mammal, the method comprising administering to the mammal an amount of a grape product effective to upregulate expression of genes that control production of detoxification enzymes in the mammal.

12. The method of embodiment 11, wherein the gene is NRF2.

13. A method of increasing production of antioxidants in a mammal, the method comprising administering to the mammal an amount of a grape product effective to increase the production of antioxidants in the mammal.

14. The method of embodiment 13, wherein the antioxidant is glutathione, superoxide dismutase, or catalase.

15. The method of any one of embodiments 1-14, wherein the grape product reduces the amount of fat deposited in the liver.

16. The method of any one of embodiments 1-15, wherein the mammal is a mammal in need thereof 17. The method of any one embodiments 1-16, wherein the grape product is whole pomace or a portion thereof, a grape seed product, a grape skin product, or any extract thereof, or any combination thereof.

18. The method of embodiment 17, wherein the grape seed product is grape seed flour.

19. The method of embodiment 17, wherein the grape product is a grape skin extract, grape skin flour, or a grape skin powder.

20. The method of embodiment 17, wherein the grape product is a pomace extract.

21. The method of embodiment 17, wherein the grape product is grape seed extract.

22. The method of embodiment 21, wherein the grape extract is a methanol or ethanol extract.

23. The method of any one of embodiments 1-22, wherein the grape product is administered in effective amount of about 1 mg to about 15,000 mg.

24. The method of any one of embodiments 1-23, wherein the mammal is a human, companion animal, domestic pet, husbanded animal, or livestock.

25. The method of any one of embodiments 1-24, wherein the method further comprises at least one additional compound.

26. The method of embodiment 25, wherein the at least one additional compound is an antioxidant, an anti-cholesterol medication, anti-glycemic compound, or an insulin sensitizer.

27. The method of embodiment 25, wherein the at least one additional compound is vitamin E, vitamin A, vitamin C, a carotenoid, lipoic acid, ubiquinol, ubiquinone, or glutathione.

28. The pharmaceutical composition of embodiment 25, wherein the at least one additional compound is s-adenosyl-methionine, trimethyl glycine, or methionine.

29. The pharmaceutical composition of embodiment 25, wherein the at least one additional compound is a phosphatide, an essential fatty acid, choline, or a B vitamin.

30. The pharmaceutical composition of embodiment 25, wherein the at least one additional compound is a botanical or an extract thereof 31. The pharmaceutical composition of embodiment 30, wherein the botanical or an extract thereof, is milk thistle, schizandra, burdock, dandelion, artichoke, turmeric, celandine, kudzu, chicory, or yellow dock, or any extract thereof 32. The method of embodiment 26, wherein the anti-glycemic compound is an insulin sensitizer.

33. The method of embodiment 32, wherein the insulin sensitizer is pioglitazone, metformin, sulfonylureas, or thiazolidinediones.

34. The method of embodiment 26, wherein the anti-cholesterol compound is a HMG-CoA reductase inhibitor.

35. The method of embodiment 34, wherein the HMG-CoA reductase inhibitor is atorvastatin, fluvastatin, lovastatin, pitavastatin, pravastatin, rosuvastatin, or simvastatin.

36. The method of embodiment 25, wherein the grape product and the additional compound are administered in concurrently or in series.

37. The method of embodiment 25, wherein the grape product and the additional compound are administered in the same formulation or in different formulations.

38. The method of any one of embodiments 1-37, wherein the mammal is on a high fat diet.

39. The method of any one of embodiments 1-37, where the mammal is on a diet comprising 30 to 50% fat by calorie content.

40. The method of any one of embodiments 1-39, wherein the grape is a Chardonnay grape.

41. The method of any one of embodiments 1-39, wherein the grape is a Cabernet Sauvignon grape, a Pinot Noir grape, a Sauvignon Blanc grape, or a White Riesling grape.

42. A pharmaceutical composition comprising a grape product and at least one additional compound.

43. The pharmaceutical composition of embodiment 42, wherein the grape product is whole pomace or a portion thereof, a grape seed product, a grape skin product, or any combination thereof, or any extract thereof 44. The pharmaceutical composition of embodiment 43, wherein the grape seed product is a grape seed flour.

45. The pharmaceutical composition of embodiment 43, wherein the grape skin product is a grape skin extract.

46. The pharmaceutical composition of any one of embodiments 42-45, wherein the grape is a Chardonnay grape, Cabernet Sauvignon grape, Pinot Noir grape, Sauvignon Blanc grape, or a White Riesling grape product.

47. The pharmaceutical composition of embodiment 42, wherein the at least one additional compound is an antioxidant.

48. The pharmaceutical composition of embodiment 42, wherein the at least one additional compound is vitamin E, obeticholic acid, 2,4-dinitrophenol (DNP), DNP-methyl ether (DNPME), an anti-glycemic compound, or an anti-cholesterol compound.

49. The pharmaceutical composition of embodiment 42, wherein the at least one additional compound is vitamin E, vitamin A, vitamin C, a carotenoid, lipoic acid, ubiquinol, ubiquinone, or glutathione.

50. The pharmaceutical composition of embodiment 42, wherein the at least one additional compound is s-adenosyl-methionine, trimethyl glycine, or methionine.

51. The pharmaceutical composition of embodiment 42, wherein the at least one additional compound is a phosphatide, an essential fatty acid, choline, or a B vitamin.
52. The pharmaceutical composition of embodiment 42, wherein the at least one additional compound is a botanical or an extract thereof
53. The pharmaceutical composition of embodiment 52, wherein the botanical or an extract thereof, is milk thistle, schizandra, burdock, dandelion, artichoke, turmeric, celandine, kudzu, chicory, or yellow dock, or any extract thereof
54. The pharmaceutical composition of embodiment 48, wherein the anti-glycemic compound is an insulin sensitizer.
55. The pharmaceutical composition of embodiment 54, wherein the insulin sensitizer is pioglitazone, metformin, thiazolidinediones, or sulfonylureas.
56. The pharmaceutical composition of embodiment 48, wherein the anti-cholesterol compound is a HMG-CoA reductase inhibitor.
57. The pharmaceutical composition of embodiment 56, wherein the HMG-CoA reductase inhibitor is atorvastatin, fluvastatin, lovastatin, pitavastatin, pravastatin, rosuvastatin, or simvastatin.
58. A method of modulating the expression of one or more of the genes in Table 3 comprising administering a grape product to a mammal expressing one or more of the genes.
59. The method of embodiment 58, wherein the gene is one or more of Chi3l1, Ces1d, Adra1b, Slc13a3, Ntrk2, Cyp21a1, Aqp8, Gck, Pfkm, Txn1, Ckb, Gckr, Fen1, Cyp46a1, Vldlr, Ppcdc, Bdh2, Scd1, Acot11, Mlxip1 (ChREBP), Lcn13, Prodh, Gstt3, Mc5r, Tas2r104, Vmn1r192, Ras12-9, Cfd, Ctse, Orm2, Rorc, Tlr5, Hnmt, Cyp2b13, Cyp2d40, Hao2, Gdf15, Sptlc3, Mogat1, Plin4, Ifna9, Asns, Got1, Atp6v0d2, Cyp7b1, Cyp17a1, Id1, Avpr1a, Ocln, Cyp51, Fdft1, Hmgcr, Hsd17b7, Insig1, Lss, Mvd, Mvk, Nsdhl, Sc4 mol, Tm7sf2, Apom, Lepr, Pcsk9, Sqle, Il17rb, Acs13, Agxt, Aldoc, Pgk2, Tlr13, Hmgcs1, Stard4, Mmp7, and Igfbp2.
60. The method of embodiment 58, wherein the grape product is a grape seed flour extract.
61. The method of embodiment 58, wherein the grape product is a grape seed flour.
62. The method of any one of embodiments 58-61, wherein the grape is a Chardonnay grape.
63. The method of any one of embodiments 58-61, wherein the grape is a Cabernet Sauvignon, Pinot Noir grape, Sauvignon Blanc grape, or a White Riesling grape.

The embodiments will not be further described with reference to the examples, which are non-limiting.

EXAMPLES

Example 1

Diet-induced (DIO) hamsters were fed a high fat (HF) diet for 10 weeks. Animals that exhibited low glucose tolerance and were in the heaviest category were given the various treatments. Animals were fed diets containing partially defatted Chardonnay flavonoid-rich wine grape seed flour (ChrSd), commercial extracts, or laboratory produced ethanolic extracts of ChrSd for 10 and 20 weeks, respectively. Half were sacrificed and examined for signs of hepatic dysfunction at 10 weeks and the other half examined after 20 weeks. Animals on treatments benefited. Animals on ChrSd whole flour treatments showed no signs of ectopic fat in the liver, whereas those on the HF Control diet showed extensive fat deposition in the liver. Livers of animals under various treatments weighed significantly less than those on the HF Control. Blood lipid profiles of animals on various grape seed treatments showed improved blood lipid profiles. Accordingly, ChrSd can be used to maintain a healthy blood lipid profile, such as when the animal is subjected to a high fat diet.

Example 2

Diet-induced obese (DIO) mice were fed high-fat (HF) diets containing either partially defatted flavonoid-rich Chardonnay grape seed flour (ChrSd) or microcrystalline cellulose (MCC, control) for 5 weeks in order to determine whether ChrSd improved insulin resistance and the pathogenesis of hepatic steatosis. The 2-h insulin and glucose areas under the curves were significantly lowered by ChrSd, indicating that ChrSd improved insulin sensitivity and glucose metabolism. ChrSd intake also significantly reduced body weight gain, liver and adipose tissue weights, hepatic lipid content, and plasma low-density lipoprotein (LDL)-cholesterol, despite a significant increase in food intake. Exon microarray analysis of hepatic gene expression revealed down-regulation of genes related to triglyceride and ceramide synthesis, immune response, oxidative stress, and inflammation, and up-regulation of genes related to fatty acid oxidation, cholesterol, and bile acid synthesis. Expression of leptin receptor was up-regulated, suggesting enhanced hepatic leptin sensitivity. Pathway analysis of the microarray data revealed that lipid and cholesterol metabolism, and infectious and metabolic disease pathways were differentially regulated by ChrSd. In conclusion, ChrSd ameliorated the effects of a HF diet on weight gain, insulin resistance, and progression of hepatic steatosis in DIO mice via modulation of hepatic expression of genes related to oxidative stress, inflammation, and lipid and cholesterol metabolism.

Animals and Diets.

Male C57BL/6J mice were housed individually in an environmentally controlled room (20-22 C, 60% relative humidity, 12-h alternating light/dark cycle). The mice were acclimated and given ad libitum access to water and mouse chow diet (LabDiet 5015, PMI International, Redwood, Calif., USA) for 1 week prior to initiation of the experimental diets. Mice were weighed and randomized into two groups of 30 mice each. Mice were fed ad libitum with either mouse chow diet or a HF diet containing 17% of energy as protein, 37% as carbohydrate, and 47% as fat, with 0.1% cholesterol. After 5 weeks, mice were weighed, and diet-induced obese (DIO) mice were identified as those having gained significantly more weight than the chow-fed mice. The DIO mice were then randomized into two groups (n=10 each) and fed ad libitum for 5 weeks with HF diets containing either 10% ChrSd (Sonomaceuticals, LLC/WholeVine Products, Santa Rosa, Calif.) or 5% microcrystalline cellulose (MCC, control diet; Dyets Inc., Bethlehem, Pa.) (Table 1). MCC, an insoluble fiber, has little effect on sterol metabolism (Horton, 1994 #56). Chardonnay grape pomace was obtained from coastal vineyards in Sonoma County, Calif. Seeds from the 2010 vintage were dried using heated air (55-70 C) and separated from skins and stems. The residual press cake was milled to pass through an 85 mesh sieve, after oil had been pressed from the seed. The total flavonoids, total catechins, catechin, and epicatechin contents of ChrSd were 12,000, 1610, 701, and 732 mg/100 g, respectively. Body weights were recorded weekly, and food intake was monitored twice per week. The study protocol, #P-04-02, was approved by the Animal Care and Use Committee, Western Regional Research Center, USDA, Albany, Calif., USA.

Plasma and Liver Collection.

Mice were feed-deprived for 12 h and anesthetized with isoflurane (Phoenix Pharmaceutical, St. Joseph, Mo., USA). Blood was collected by cardiac puncture with syringes previously rinsed with potassium EDTA solution (15% w/v). The plasma was separated after centrifugation at 2,000×g for 30 min at 4 C. Livers and epididymal adipose tissues were collected, weighed, and immediately frozen in liquid nitrogen for later analysis. After freeze-drying, the powdered livers were weighed and mixed with 2 mL of $CHCl_3$/MeOH (2:1), sonicated for 5 min, and then incubated overnight. The samples were centrifuged for 10 min at 1000 rpm, and the supernatant was removed. Another 2 mL of $CHCl_3$/MeOH was added, sonicated, and allowed to stand overnight to extract. Solvent was removed from the combined extracts under nitrogen and the total hepatic total lipid content was determined gravimetrically.

Plasma Lipid Analysis.

Plasma lipoprotein cholesterol was determined by size exclusion chromatography. Briefly, high-performance liquid chromatograpy (HPLC) was carried out using an Agilent 1100 HPLC chromatograph with a Superose 6HR HPLC column (Pharmacia LKB Biotechnology, Piscataway, N.J., USA) consisting of a mixing coil (1615-50 Bodman, Aston, Pa., USA) in a temperature-controlled water jacket (Aura Industrials, Staten, N.Y., USA). A Hewlett-Packard HPLC pump (79851-A; Agilent Technologies, Palo Alto, Calif., USA) was used to deliver cholesterol reagent (Roche Diagnostics, Indianapolis, Ind., USA) at a flow rate of 0.2 mL/min. Bovine cholesterol lipoprotein standards were used to calibrate the signal on the basis of peak areas.

Glucose Tolerance Test (GTT) and Insulin Tolerance Test (ITT).

After a 3-h fast, mice were administrated glucose intraperitoneally (2 g/kg body weight), and tail vein blood glucose levels were determined at 0, 15, 30, 60, and 120 min after glucose injection using a OneTouch Ultrameter (LifeScan Inc., Wayne, Pa.). ITT was performed after mice were administrated insulin intraperitoneally (0.5 U/kg body weight). Glucose levels were determined in tail vein blood at 0, 30, and 60 min after insulin injection using a OneTouch Ultrameter (LifeScan Inc.).

Gene Expression and Exon Microarray Analysis.

Total liver RNA was extracted from three biological replicates within each group using a TRIzolplus RNA purification kit (Invitrogen, Life Technologies, Carlsbad, Calif., USA). The total RNA quality was determined using a 2100 Bioanalyzer instrument and RNA 6000 Nano LabChip assay (Agilent Technologies, Palo Alto, Calif., USA). Total RNA (10 µg) was then used to synthesize one-cycle cDNA (first-strand and second-strand cDNA synthesis) followed by clean-up of double-stranded cDNA, and biotin-labeled cRNA synthesis. The biotin-labeled cRNA was fragmented using One-Cycle Target Labeling and Control reagents (Affymetrix, Santa Clara, Calif., USA). Fragmented cRNA samples were hybridized to an Affymetrix GeneChip Mouse exon 1.0 ST array, an expression and exon splicing array containing 1.2 million probe sets, representing 80000 genes. The hybridization signals were acquired and analyzed using the GeneChip Scanner 3000 High-Resolution Scanner (Affymetrix) and the Affymetrix GeneChip Operating Software (GCOS). Analysis of both gene expression and exon alternative splicing from the microarray data was performed using a GeneSpring GX version 11.0 program (Agilent Technologies, Santa Clara, Calif.). Gene expression was determined to be significant when the change was found to be 1.5-fold and above. The splice index was defined as the log of the ratio of exon-level expression over gene-level expression. A fold change in splice index value≥2 between treatment and control groups was considered to be differentially spliced. Transcripts with at least one differentially spliced exon were considered to be differentially regulated splicing.

Statistical Analysis.

All data were expressed as means±SE. Analysis of variance (ANOVA) was performed using the JMP7 statistical program (SAS Institute, Cary, N.C., USA) to examine the effects of treatment on plasma lipid levels, body and tissue weights, total energy intake, and feed efficiency ratio. Significance was defined at $P<0.05$. Ingenuity Pathways Analysis tool (IPA version 8.7, Ingenuity Systems Inc., Redwood City, Calif., USA; http://www.ingenuity.com) was used to analyze the exon microarray data determining biological mechanisms, pathways, and functions from the differentially expressed genes. Right-tailed Fisher's exact test was used to calculate the P value. P values represent the probability that the biological function of each data set, biological function and disease assigned to a particular network for each data set, and the association between the genes in a data set and the corresponding canonical pathway were explained by chance.

Metabolic Effects.

Figure 2A:
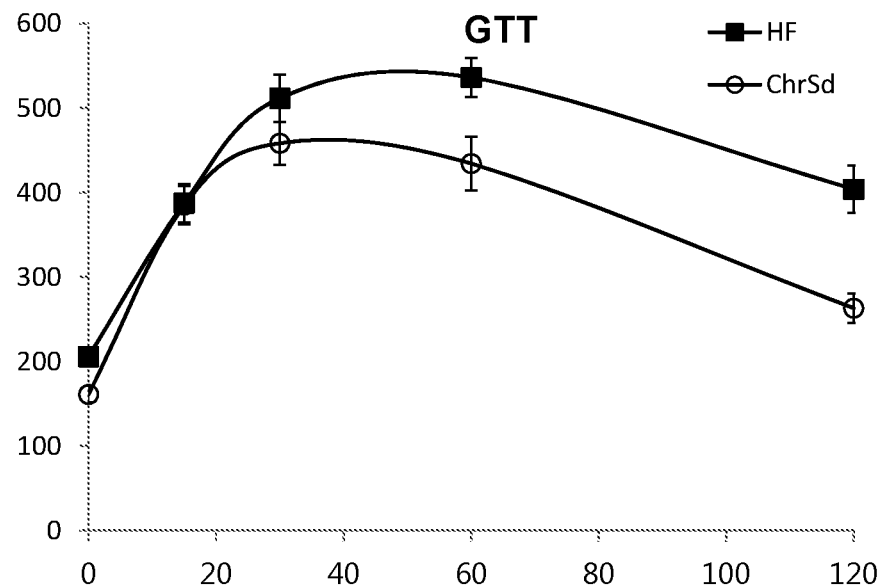
FIGS. 2A and 2B.
Figure 2B:
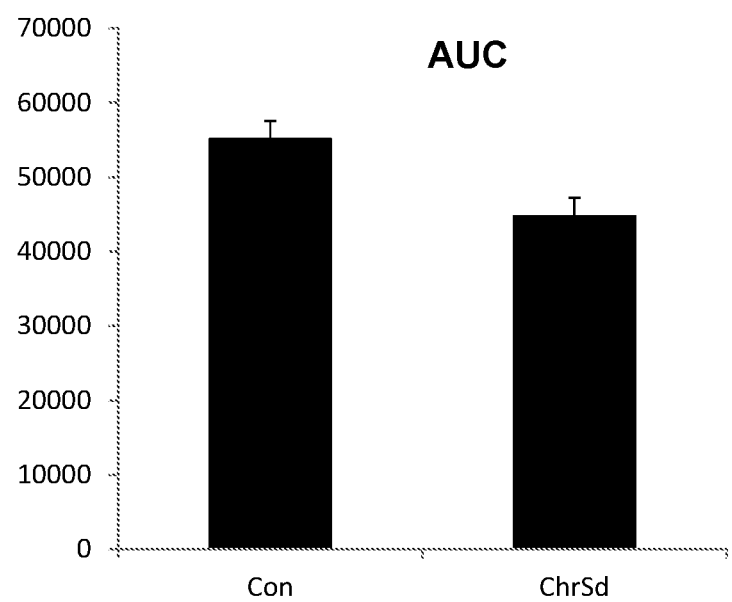
Figure 3A:
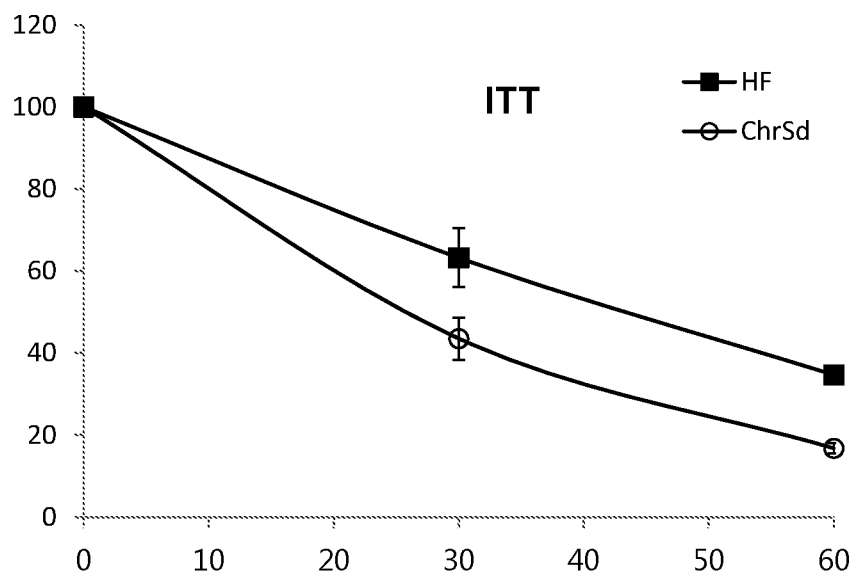
FIGS. 3A and 3B.
Figure 3B:
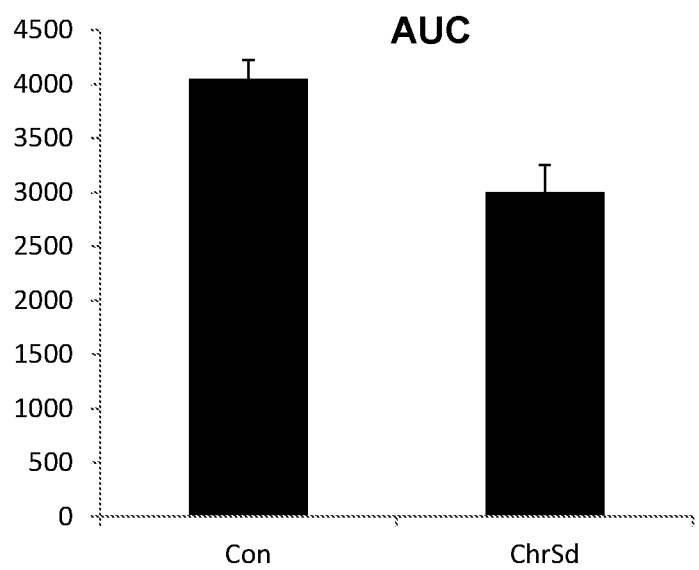

ChrSd supplementation of a HF diet for 5 weeks significantly lowered body weight gain of the DIO mice despite a significant increase of total energy intake, resulting in a 72% lower energy efficiency ratio in these mice (Table 2). The ChrSd supplemented diet significantly lowered the liver and epididymal adipose tissue weights by 38% and 35%, respectively, as compared with mice on the control diet (Table 2). Total hepatic lipid content was 43% lower in DIO mice fed ChrSd, as compared to control diet ($P<0.05$) (Table 2). Dietary ChrSd supplementation significantly lowered peak blood glucose response at 60 min ($P<0.05$) and the area under the curve (AUC) during a 2-h glucose response (FIGS. 2A and B). ChrSd supplementation also resulted in a marked reduction of insulin response at 30 min ($P<0.05$) and 60 min ($P<0.05$) (FIGS. 3A and B).

Microarray Analysis of Hepatic Gene Expression Profiles

The comprehensive expression of hepatic genes in DIO mice fed HF diets supplemented with either 5% MCC or 10% ChrSd flour was assessed by exon microarray analysis. A number of genes were differentially expressed in mice fed 10% ChrSd, as compared to those fed 5% MCC ($P<0.05$, fold change ≥1.5) (Table 3). Among these genes, some were down-regulated and some were up-regulated. Table 3 shows the genes differentially down- and up-regulated by ChrSd, categorized by biological process. Chitinase-like 1(Chi3l1; fold change, −1.5), encoding a protein involved in the activation of nuclear factor-kappaB (NF-κB)-induced kinase activity, involved in inflammation and tissue remodeling, was down-regulated. A gene encoding an enzyme involved in cortiscosteroid biosynthesis (C21-steroid hormone biosynthesis, cytochrome P450, family 21, subfamily a polypeptide 1 (Cyp21a1; fold change, −1.6)) was down-regulated. The expression level of aquaporin 8 (Aqp8; fold change, −1.8), encoding a protein related to canalicular bile acid transport was down-regulated. Genes encoding proteins involved in diacylglycerol and triacylglycerol biosynthetic processes (stearoyl-coenzyme A desaturase 1 [Scd1]; monoacylglycerol O-acyltransferase 1 [Mogat1]) were down-regulated (fold change, −1.6 for both). Expression of odorant binding protein 2A (Lcn13), involved in glucose and lipid metabolism, was down-regulated (fold change, −3.5). Genes involved in immune system processes, including complement factor D (Cfd; fold change, −2.4), cathepsin E (Ctse; fold change, −1.7), orosomucoid 2 (Orm2, fold change, −1.7), retinoic acid receptor-related orphan receptor gamma (Rorc; fold change −1.5), and toll-like receptor 5 (Tlr5; fold change, −2) were down-regulated. Serine palmitoyltransferase, long chain base subunit 3 (Sptlc3; fold change, −1.7), which is involved in sphingolipid metabolism, was down-regulated. Expression of a lipid droplet-associated protein involved in triglyceride metabolic process, perilipin 4 (Plin4; fold change, −3.5), was also down-regulated in mice fed ChrSd, as compared to mice fed MCC. Interferon alpha 9 (Ifna9; fold change, 1.8), a gene encoding a protein related to host immune defense response, was up-regulated. The expression of genes encoding cytochrome P450, family 7, subfamily b, polypeptide 1 (Cyp7b1; fold change, 1.6) and cytochrome P450, family 17, subfamily a, polypeptide 1 (Cyp17a1; fold change, 2.5), related to bile acid metabolism, was up-regulated. Genes involved in cholesterol metabolism, including sterol 14-demethylase (Cyp51; fold change, 5.6), 3-hydroxy-3-methylglutaryl-coenzyme A reductase (Hmgcr; fold change, 2.5), hydroxysteroid (17-β) dehydrogenase 7 (Hsd17b7; fold change, 2.8), insulin induced gene 1 (Insig1; fold change, 1.8), sterol-C4-methyl oxidase-like (Sc4 mol; fold change, 4.5), and leptin receptor (Lepr; fold change, 1.6) were up-regulated. The expression level of acyl-CoA synthetase long-chain family member 3 (Acsl3), which is involved in fatty acid β-oxidation, was up-regulated.

Pathway analysis using the IPA System identified several biological functions and canonical gene pathways that were differentially regulated by ChrSd supplementation (Table 4). When grouped by biological function, the expression levels of genes related to lipid metabolism, hematological disease, and metabolic disease were significantly affected by ChrSd supplementation. In terms of canonical pathways, ChrSd affected the cholesterol biosynthesis superpathway and the zymosterol biosynthetic pathway. Networks involving lipid metabolism and infectious disease were affected by ChrSd supplementation. Insig1, which regulates cholesterol concentration, was identified as a major regulator effects networks (data not shown). Analysis of exon microarray data using the GeneSpring GX11.0 program resulted in the identification of 84 genes with SI>|2.0| in the presence of ChrSd supplementation (data not shown). Further analysis by using RT-PCR needs to be done to confirm the alternative splicing of these genes.

In the current study, exon microarray analysis was used to identify differentially expressed hepatic genes in DIO mice, to provide novel biological insights into the effects of ChrSd supplementation on HF diet-induced hepatic steatosis. We found that, in addition to affecting expression of genes involved in cholesterol, bile acid, and lipid metabolism, dietary ChrSd supplementation significantly affected the hepatic expression of genes involved in C21-steroid metabolism, immune system processes, inflammation, tissue remodeling, and lipid storage. ChrSd supplementation markedly up-regulated hepatic expression of genes related to bile acid and cholesterol synthesis (Cyp17a1, Cyp51, Hmgcr, and Insig1), and fatty acid β-oxidation (Acsl3), whereas it significantly down-regulated the expression of genes related to fatty acid biosynthesis (Scd1, Acot11, and Mlxipl/carbohydrate responsive element-binding protein [ChREBP]), triacylglycerol biosynthesis (Mogat1), oxidative stress (Growth differentiation factor 15, Gdf15), inflammatory and immune processes (Cfd, Chi3l1, Ctse, Orm2, Rorc, and Tlr5), ceramide biosynthesis (Sptlc3), and lipid storage (Plin4). These altered gene expression profiles in hepatic tissue were accompanied by significant reductions in plasma LDL-cholesterol concentration, liver, adipose, and body weights, feed efficiency ratio, and insulin resistance, as compared to the MCC supplemented control group. Notably, ChrSd supplementation lowered the hepatic expression of genes that have a role in obesity including Insig-1, lepR, Neurotrophic tyrosine kinase, receptor, type 2 (Ntrk2), Melanocortin 5 receptor (Mc5r), and Matrix metallopeptidase 7 (Mmp7).

Without being bound by any particular theory, we hypothesize that supplementation with ChrSd containing high amounts of flavonoids can up-regulate genes related to scavenging of reactive oxygen species (ROS) and free radicals, and down-regulate genes related to oxidative stress, inflammation, and fatty acid biosynthesis, leading to improved HF-induced insulin resistance and NAFLD. The suggested mechanisms involved in the antioxidant activity of flavonoids are: 1) free radical scavenging and metal chelating activities; 2) cell-to-cell signaling pathways; and 3) antioxidant enzyme gene expression. The antioxidant activity of grape seed products has been monitored in in vitro. The in vivo biological significance of in vitro activity is not clear because oligomers and larger flavonoids are poorly absorbed, while monomers are rapidly metabolized and cleared from the body. In the present study, expression of stress responsive genes (Gdf15 and ChREBP) was down-regulated following ChrSd supplementation. The hepatic expression of Gdf15, a member of the transforming growth factor (TGF) superfamily, is related to hepatic steatosis under ER stress. Oxidative stress activates ChREBP, which transcriptionally modulates lipogenic and glycolytic genes, resulting in fatty liver. Taken together, these findings indicated that the flavonoid-rich ChrSd supplement can potentiate antioxidant activity and reduce oxidative stress, resulting in transcriptional down-regulation of ChREBP and lipogenic genes (Scd1, Acot11, Mogat1) in the liver. Despite the down-regulation of stress related genes, the canonical pathway analysis did not identify significant changes in the free radical and ER stress-related signaling pathways in the livers of DIO mice supplemented with ChrSd. Oxidative stress and inflammation are closely interlinked in obesity. However, whether improved oxidative stress and inflammation are secondary to or independent of reduction in hepatic lipid levels is not clear. Additionally, we cannot exclude the possibility that C57BL/6J mice fed a HF diet (47% of energy as fat) for 10 weeks may have already passed through the obesity-related ER stress response and entered the lipogenesis stage. This transition from ER stress to lipogenesis was shown in a previous study of ApoE3L mice on HF diets for 16 weeks; these animals exhibited an early phase hepatic response to the HF diet that was characterized by changes in genes linked to the stress pathways, followed by a late phase involving genes related to lipid accumulation. Likewise, the present study found few ChrSd-induced changes of genes related to free radicals and ER-stress response.

The C57BL/6J mouse has been used extensively to study hepatic steatosis. This animal model shows more susceptibility to HF diet-induced fatty liver disease than BALB/c mice. Genes related to the 26S proteasome and ubiquitin proteasome system in wild type C57BL/6J mice fed HF diets (40% energy as fat) for 15 weeks were up-regulated relative to transgenic mice with lowered proteasome activity, resulting in obesity and hepatic steatosis. In contrast, no significant modulation of genes related to ER-stress and inflammation was observed. In another study, C57BL/6J mice fed a HF diet (60% of energy as fat) developed hepatic steatosis and inflammation after 24 weeks. In the present study, we selected obesity responsive mice by feeding HF diet for 5 weeks and then selecting DIO mice for treatment with HF diets supplemented with either ChrSd or MCC (control) for an additional 5 weeks. The lower degree of free radical scavenging response may be due to the shorter duration of the ChrSd supplementation phase of the study and the lower level of dietary fat, as compared to previous studies showing an oxidative stress response.

Flavonoids have been reported to show immunomodulatory and anti-inflammatory properties, although most of these studies have been conducted in vitro, with very few in vivo or human analyses. In humans, the consumption of 600 mg/day grape seed extract for 4 weeks improved markers of insulin resistance (e.g. blood C-reactive protein [CRP] concentration) and inflammation in type 2 diabetic patients at high risk for cardiovascular disease. In this study, ChrSd supplementation down-regulated hepatic expression of genes related to immune and inflammation processes (Cfd, Chi3l1, Ctse, Orm2, Rorc, Tlr5). Cfd (adipsin) is a serine protease involved as a host response factor in the removal of foreign antigens and pathogens. The Chi3l1 gene is related to activation of NF-κB-induced kinase activity and inflammation. Ctse is an intracellular aspartic proteinase highly expressed in immune-related cells, such as macrophages, and its main role is related to macrophage infiltration, adipogenesis, and hepatic steatosis. Orm2 is expressed in hepatocytes and adipocytes, and secreted into plasma under metabolic and inflammatory stress as an acute phase reactant immunomodulator protein. Rorc regulates Th17 cell differentiation, controlling the production of inflammatory cytokines. Tlr5 is predominantly expressed in epithelial cells of the intestinal mucosa and its expression in liver and adipose tissue is relatively very low. Interestingly, HF diet has been shown to increase Tlr5 expression in mouse epididymal adipose tissue. It is activated by bacterial flagellin proteins and triggers innate immune responses and NF-κB. Although the biological significance of hepatic Tlr5 down-regulation is unclear, ChrSd supplementation may reduce the gut bacterial residence-derived inflammatory response to HF-induced stress. Our previous study suggested that hepatic cholesterol metabolism was influenced by the composition of intestinal microbiota and by intestinal fibroblast growth factor (FGF) 15 gene expression in hamsters following ChrSd supplementation. Collectively, these findings indicate that ChrSd supplementation may prevent HF diet-induced inflammation in the liver via down-regulation of hepatic expression of genes related to immune/inflammatory pathways.

ChrSd supplementation up-regulated hepatic leptin receptor expression by 1.5-fold, as compared with control. Leptin, a hormone produced by adipose tissue, regulates energy intake and expenditure and enhances fatty acid oxidation in liver and muscle. In DIO mice, down-regulation of hepatic leptin receptor expression was observed, suggesting that obesity induces hepatic insensitivity to leptin. Thus, the ChrSd-associated up-regulation in hepatic leptin receptor expression suggested that hepatic leptin sensitivity was improved by this supplement and this could, in part, contribute to reduced hepatic steatosis.

Several studies have suggested that oxidative stress may play an important role in the development of obesity-related complications such as insulin resistance and type 2 diabetes. Consumption of red grape extract improved fructose-induced ER-stress and insulin sensitivity in healthy overweight first-degree relatives of type 2 diabetic patients. Similarly, our study revealed that supplementation with the flavonoid-rich ChrSd significantly improved insulin sensitivity and glucose metabolism, as shown by the 26% and 19% reductions in AUC during 2-h ITT and GTT, respectively, as compared to the control. ChrSd supplementation also significantly lowered the fasting glucose concentration. Additionally, this improved insulin sensitivity was paralleled by down-regulation of hepatic Gdf15 expression. Gdf15 expression has been reported to be induced in response to oxidative stress and inflammation, and its levels are increased in individuals with abdominal obesity, CVD, and insulin resistance. It has been shown that suppression of the hepatic expression of genes related to inflammatory and immune processes was associated with improved liver function of HF-induced fatty liver. On the other hand, lipid derivatives such as ceramides are a critical modulator of cellular stress and their accumulation inhibits insulin signaling. It has been shown that flavonoids influence sphingolipid metabolism and are able to normalize the elevated ceramide content of damaged liver cells. These observations indicated a potential connection between the ChrSd-related down-regulation of hepatic Sptlc3, a gene related to ceramide biosynthesis, and the reduced hepatic lipid content and improved insulin sensitivity reported in the present study. Therefore, improved insulin resistance and reduced hepatic lipid content appeared to be mediated by a reduction in oxidative stress and inflammation in DIO mice supplemented with ChrSd.

Glucokinase (Gck) activation may induce fatty liver in rodents because this enzyme phosphorylates glucose to produce glucose-6-phosphate; this regulates hepatic glucose disposal and stimulates hepatic lipogenesis. Recent studies have shown that Gck overexpression in the liver increases hepatic lipogenesis and circulating lipid concentrations. Furthermore, hepatic Gck expression was associated with hepatic lipogenic gene expression and the lipid content of human liver biopsies. ChrSd supplementation down-regulated hepatic expression of Gck and Gckr (glucokinase regulatory protein) and this may also have contributed to reducing the HF-induced hepatic lipid content.

In summary, it has been demonstrated herein that flavonoid-rich ChrSd, a byproduct of winemaking, improved HF-induced hepatic steatosis, plasma lipid profiles, and weight gain, as well as insulin resistance. These improvements were associated with modulation of the hepatic expression of genes related to bile acid, cholesterol, and fatty acid metabolism, oxidative stress, inflammation, and immune responses. Analysis of exon microarray data revealed that pathways involved in lipid and cholesterol metabolism, and infectious and metabolic disease were differentially regulated by ChrSd. The decreased feed efficiency ratio, and reductions in hepatic lipid content, adipose tissue weight, hepatic ceramide synthesis, and oxidative stress may have contributed to the observed improvement in insulin sensitivity. These results indicate that consumption of flavonoid-rich ChrSd can be beneficial for the prevention and/or treatment of NAFLD and other metabolic diseases due to its reduction of oxidative stress and inflammation, modulation of cholesterol and bile acid synthesis, modulation of lipid metabolism in liver, and amelioration of insulin resistance, as well as promotion of overall liver health.

TABLE 1

Diet Composition

| Ingredient (g/kg) | Con | ChrSd |
|---|---|---|
| Lard fat | 225.0 | 225.0 |
| Soybean oil | 25.0 | 12.3 |
| Cholesterol | 0.8 | 0.8 |
| MCC | 52.6 | 18.6 |
| Char seed | 0 | 100.0 |
| Casein | 200.0 | 182.5 |
| Corn starch | 145.6 | 109.8 |
| Sucrose | 300.0 | 300.0 |
| DL methionine | 3.0 | 3.0 |
| Choline bitartrate | 3.0 | 3.0 |
| Mineral mix | 35.0 | 35.0 |
| Vitamin mix | 10.0 | 10.0 |
| Total weight | 1000.0 | 1000.0 |
| Calories/kg | 4444 | 4427 |

Con (Control diet containing 5% MCC, microcrystalline cellulose);
ChrSd containing 10% Chardonnay grape seed flour

TABLE 2

Anthropometrics in DIO mice fed MCC and ChrSd for 5 wk[1]

|  | Con | ChrSd |
|---|---|---|
| Body weight gain (g) | 2.4 ± 0.6 | −2.0 ± 0.7* |
| Total energy intake (Kcal) | 676.0 ± 13.3 | 784.1 ± 20.1* |
| Feed efficiency ratio (g gain/g feed) | 0.18 ± 0.00 | −0.13 ± 0.00* |
| Liver weight (g) | 1.6 ± 0.2 | 1.0 ± 0.1* |
| Epididymal adipose tissue weight (g) | 2.0 ± 0.1 | 1.3 ± 0.1* |
| Hepatic percent total lipid content (g/100 g) | 22.6 ± 2.2 | 12.8 ± 0.7* |

[1]Values are means ± SE, n = 10.
*indicate significant difference at $P < 0.05$.

TABLE 3

Summary of selected genes showing significant ≥|1.5|-fold hepatic modulation in mice fed a HF diet supplemented with ChrSd

| Biological Process (GO)[a] | Gene Symbol | Name | Fold-Change | Gene ID |
|---|---|---|---|---|
| Down-regulated | | | | |
| Activation of nuclear factor-kappaB-inducing kinase activity | Chi3l1 | Chitinase-like 1 | −1.5 | NM_007695 |
| Acyl-CoA metabolic process | Ces1d | Carboxylesterase 1D | −1.6 | NM_053200 |
| Adrenergic receptor signaling pathway | Adra1b | Adrenergic receptor, alpha 1b | −1.6 | ENSMUST00000067258 |
| Aspartate transport | Slc13a3 | Solute carrier family 13 (sodium-dependent dicarboxylate transporter), member 3 | −1.7 | ENSMUST00000029208 |
| Brain-derived neurotrophic factor receptor signaling pathway | Ntrk2 | Neurotrophic tyrosine kinase, receptor, type 2 | −3.4 | ENSMUST00000079828 |
| C21-steroid hormone biosynthetic process | Cyp21a1 | Cytochrome P450, family 21, subfamily a, polypeptide 1 | −1.6 | ENSMUST00000025223 |
| Canalicular bile acid transport | Aqp8 | Aquaporin 8 | −1.8 | NM_007474 |
| Carbohydrate metabolic process | Gck | Glucokinase | −3.1 | ENSMUST00000102920 |
| Carbohydrate phosphorylation | Pfkm | Phosphofructokinase, muscle | −1.6 | NM_001163487 |
| Cell redox homeostasis | Txn1 | Thioredoxin 1 | −1.5 | NM_011660 |
| Cellular chloride ion homeostasis | Ckb | Creatine kinase, brain | −1.7 | NM_021273 |
| Cellular glucose homeostasis | Gckr | Glucokinase regulatory protein | −1.8 | NM_144909 |
| Cellular response to DNA damage stimulus | Fen1 | Flap structure specific endonuclease 1 | −2 | ENSMUST00000156291 |
| Cholesterol metabolic process | Cyp46a1 | Cytochrome P450, family 46, subfamily a, polypeptide 1 | −2.2 | NM_010010 |
| | Vldlr | Very low density lipoprotein receptor | −1.7 | ENSMUST00000167487 |
| Coenzyme A biosynthetic process | Ppcdc | Phosphopantothenoylcysteine decarboxylase | −1.5 | NM_176831 |
| Degradation of ketone body | Bdh2 | 3-hydroxybutyrate dehydrogenase, type 2 | −1.6 | NM_001172055 |
| Fatty acid biosynthetic process | Scd1 | Stearoyl-Coenzyme A desaturase 1 | −1.6 | NM_009127 |

TABLE 3-continued

Summary of selected genes showing significant ≥|1.5|-fold hepatic modulation in mice fed a HF diet supplemented with ChrSd

| Biological Process (GO)[a)] | Gene Symbol | Name | Fold-Change | Gene ID |
|---|---|---|---|---|
| Fatty acid metabolic process | Acot11 | Acyl-Coenzyme A thioesterase 11 | −2.2 | NM_025590 |
| Glucose homeostasis | Mlxipl (ChREBP) | MLX interacting protein-like | −1.6 | NM_021455 |
| Glucose and lipid metabolism | Lcn13 | Odorant binding protein 2A | −3.5 | ENSMUST00000077667 |
| Glutamate biosynthetic process | Prodh | Proline dehydrogenase | −1.6 | ENSMUST00000003620 |
| Glutathione metabolic process | Gstt3 | Glutathione S-transferase, theta 3 | −1.7 | NM_133994 |
| G-protein coupled receptor signaling pathway | Mc5r | Melanocortin 5 receptor | −1.6 | NM_013596 |
|  | Tas2r104 | Taste receptor, type 2, member 104 | −1.5 | NM_207011 |
|  | Vmn1r192 | Vomeronasal 1 receptor 192 | −2.1 | NM_145845 |
| GTP catabolic process | Rasl2-9 | RAS-like, family 2, locus 9 | −2.2 | NM_009028 |
| Immune system process |  |  |  |  |
| (Innate immune response) | Cfd | Complement factor D (adipsin) | −2.4 | NM_013459 |
| (antigen processing and presentation of exogenous peptide antigen via MHC class II) | Ctse | Cathepsin E | −1.7 | NM_007799 |
| (Acute phase response) | Orm2 | Orosomucoid 2 | −1.7 | NM_011016 |
| (Regulation of gamma-delta T cell differentiation) | Rorc | Retinoic acid receptor-related orphan receptor gamma | −1.5 | NM_011281 |
| (Defense response to bacterium) | Tlr5 | Toll-like receptor 5 | −2 | NM_016928 |
| Methylation | Hnmt | Histamine N-methyltransferase | −1.5 | NM_080462 |
| Oxidation-reduction process | Cyp2b13 | Cytochrome P450, family 2, subfamily b, polypeptide 1 | −3.4 | NM_007813 |
|  | Cyp2d40 | Cytochrome P450, family 2, subfamily d, polypeptide 40 | −1.8 | ENSMUST00000055721 |
|  | Hao2 | Hydroxy acid oxidase 2 | −1.7 | NM_019545 |
| Stress-responsive cytokine | Gdf15 | Growth differentiation factor 15 | −2 | ENSMUST00000003808 |
| Sphingolipid metabolic process (Ceramide de novo synthesis) | Sptlc3 | Serine palmitoyltransferase, long chain base subunit 3 | −1.7 | ENSMUST00000110083 |
| Triacylglycerol biosynthetic process | Mogat1 | Monoacylglycerol O-acyltransferase 1 | −1.6 | NM_026713 |
| Triglyceride metabolic process | Plin4 | Perilipin 4 | −3 | NM_020568 |
| Up-regulated |  |  |  |  |
| Adaptive immune response (host immune defense) | Ifna9 | Interferon alpha 9 | 1.8 | NM_010507 |
| Asparagine biosynthetic process | Asns | Asparagine synthetase | 2.8 | ENSMUST00000031766 |
|  | Got1 | Glutamate oxaloacetate transaminase 1, soluble | 2 | NM_010324 |
| ATP hydrolysis coupled proton transport | Atp6v0d2 | ATPase, H+ transporting, lysosomal V0 subunit D2 | 2.2 | ENSMUST00000029900 |
| Bile acid biosynthetic process | Cyp7b1 | Cytochrome P450, family 7, subfamily b, polypeptide 1 | 1.6 | NM_007825 |
|  | Cyp17a1 | Cytochrome P450, family 17, subfamily a, polypeptide 1 | 2.5 | NM_007809 |
| Bone morphogenetic protein signaling pathway | Id1 | Inhibitor of DNA binding 1 | 1.7 | NM_010495 |

TABLE 3-continued

Summary of selected genes showing significant ≥|1.5|-fold hepatic modulation in mice fed a HF diet supplemented with ChrSd

| Biological Process (GO)[a] | Gene Symbol | Name | Fold-Change | Gene ID |
|---|---|---|---|---|
| Calcium-mediated signaling | Avpr1a | Arginine vasopressin receptor 1A | 2.1 | NM_016847 |
| Cell-cell junction organization | Ocln | Occludin | 1.5 | ENSMUST00000069756 |
| Cholesterol biosynthetic process | Cyp51 | Sterol 14-demethylase | 5.6 | NM_020010 |
| | Fdft1 | Farnesyl diphosphate farnesyl transferase 1 | 1.9 | NM_010191 |
| | Hmgcr | 3-Hydroxy-3-methylglutaryl-Coenzyme A reductase | 2.5 | NM_008255 |
| | Hsd17b7 | Hydroxysteroid (17-beta) dehydrogenase 7 | 2.8 | NM_010476 |
| | Insig1 | Insulin induced gene 1 | 1.8 | NM_153526 |
| | Lss | Lanosterol synthase | 2.1 | ENSMUST00000048678 |
| | Mvd | Mevalonate (diphospho) decarboxylase | 2.3 | NR_028354 |
| | Mvk | Mevalonate kinase | 2.2 | ENSMUST00000043760 |
| | Nsdhl | NAD(P) dependent steroid dehydrogenase-like | 2 | NM_010941 |
| | Sc4mol | Sterol-C4-methyl oxidase-like | 4.5 | ENSMUST00000034015 |
| | Tm7sf2 | Transmembrane 7 superfamily member 2 | 1.7 | NM_028454 |
| Cholesterol efflux | Apom | Apolipoprotein M | 1.6 | ENSMUST00000025249 |
| Cholesterol metabolic process | Lepr | Leptin receptor | 1.6 | NM_146146 |
| | Pcsk9 | Proprotein convertase subtilisin/kexin type 9 | 1.9 | NM_153565 |
| | Sqle | Squalene epoxidase | 13.5 | NM_009270 |
| Cytokine-mediated signaling pathway | Il17rb | Interleukin 17 receptor B | 1.5 | NM_019583 |
| Fatty acid β-oxidation | Acsl3 | Acyl-Coenzyme A synthetase long-chain family member 3 | 1.9 | NM_028817 |
| Glycine biosynthetic process, by transamination of glyoxylate | Agxt | Alanine-glyoxylate aminotransferase | 1.5 | NM_016702 |
| Glycolytic process | Aldoc | Aldolase C, fructose-bisphosphate | 2.2 | ENSMUST00000017534 |
| | Pgk2 | Phosphoglycerate kinase 2 | 1.6 | NM_031190 |
| Inflammatory response | Tlr13 | Toll-like receptor 13 | 1.6 | ENSMUST00000040065 |
| Lipid metabolic process | Hmgcs1 | 3-Hydroxy-3-methylglutaryl-Coenzyme A synthase 1 | 2.2 | NM_145942 |
| Lipid transport | Stard4 | StAR-related lipid transfer (START) domain containing 4 | 1.9 | ENSMUST00000025236 |
| Proteinaceous extracellular matrix | Mmp7 | Matrix metallopeptidase 7 | 1.5 | ENSMUST00000018767 |
| Regulation of insulin-like growth factor 1 receptor signaling pathway | Igfbp2 | Insulin-like growth factor binding protein 2 | 2.3 | NM_008342 |

[a] Genes were classified into biological process categories according to Gene Ontology Consortium (GO) classification.

TABLE 4

The top 10 biological functions and top 5 canonical and network pathways of genes significantly modulated by ChrSd

| Biological Function | P value | No. of genes differentially expressed |
|---|---|---|
| Lipid Metabolism | $2.87 \times 10^{-10}$-$3.11 \times 10^{-2}$ | 48 |
| Small Molecule Biochemistry | $2.87 \times 10^{-10}$-$3.23 \times 10^{-2}$ | 64 |
| Vitamin and Mineral Metabolism | $2.87 \times 10^{-10}$-$2.09 \times 10^{-2}$ | 21 |
| Molecular Transport | $2.52 \times 10^{-7}$-$3.23 \times 10^{-2}$ | 39 |
| Cell Morphology | $6.92 \times 10^{-4}$-$3.11 \times 10^{-2}$ | 15 |
| Hematological Disease | $5.48 \times 10^{-4}$-$3.12 \times 10^{-2}$ | 13 |
| Metabolic Disease | $5.48 \times 10^{-4}$-$3.11 \times 10^{-2}$ | 25 |
| Neurological Disease | $6.17 \times 10^{-4}$-$3.11 \times 10^{-2}$ | 35 |
| Psychological Disorders | $6.17 \times 10^{-4}$-$3.11 \times 10^{-2}$ | 27 |
| Dermatological Diseases and Conditions | $1.14 \times 10^{-3}$-$1.05 \times 10^{-2}$ | 18 |

TABLE 4-continued

The top 10 biological functions and top 5 canonical and network pathways of genes significantly modulated by ChrSd

| Canonical Pathway | P value | Ratio[a] |
|---|---|---|
| Superpathway of Cholesterol Biosynthesis | $1.81 \times 10^{-17}$ | 12/87 (0.138) |
| Cholesterol Biosynthesis I | $1.53 \times 10^{-13}$ | 8/40 (0.2) |
| Cholesterol Biosynthesis II (via 24,25-dihydrolanosterol) | $1.53 \times 10^{-13}$ | 8/40 (0.2) |
| Cholesterol Biosynthesis III (via Desmosterol) | $1.53 \times 10^{-13}$ | 8/40 (0.2) |
| Zymosterol Biosynthesis | $7.12 \times 10^{-10}$ | 5/22 (0.227) |

| Network Pathway | Sore[b] |
|---|---|
| Lipid Metabolism, Small Molecule Biochemistry, Vitamin and Mineral Metabolism | 58 |
| Infectious Disease, Organismal Injury and Abnormalities, Renal and Urological Disease | 36 |
| Protein Synthesis, Carbohydrate Metabolism, Lipid Metabolism | 36 |
| Lipid Metabolism, Small Molecule Biochemistry, Vitamin and Mineral Metabolism | 33 |
| Behavior, Neurological Disease, Endocrine System Development and Function | 29 |

The functions and pathways that were most significant to the dataset were identified by Ingenuity Pathway Analysis (Ingenuity Systems).
[a] Number of molecules (genes) that met the cut-off criteria, divided by the total number of molecules within a given pathway.
[b] Likelihood of finding the focus molecules in a given pathway, expressed as the negative log of the P value.

While the embodiments have been depicted and described by reference to exemplary embodiments, such a reference does not imply a limitation on the scope, and no such limitation is to be inferred. The embodiments are capable of considerable modification, alteration, and equivalents in form and function, as will occur to those ordinarily skilled in the pertinent arts having the benefit of this disclosure. All references cited herein are hereby incorporated by reference in their entirety and for their intended purpose.

What is claimed is:

1. A method of treating non-alcoholic fatty liver disease (NAFLD) or non-alcoholic steatohepatitis (NASH) in a mammal in need thereof, comprising administering to the mammal an amount of a Pinot Noir grape seed flour effective to treat NAFLD or NASH.

2. The method of claim 1, wherein the Pinot Noir grape seed flour reduces the amount of fat deposited in the liver.

3. The method of claim 1, wherein the Pinot Noir grape seed flour is administered in effective amount to treat NAFLD or NASH of about 1 mg to about 15,000 mg.

4. The method of claim 1, wherein the mammal is a human, companion animal, domestic pet, husbanded animal, or livestock.

5. The method of claim 1, wherein the method further comprises at least one additional compound.

6. The method of claim 5, wherein the at least one additional compound is an antioxidant, an anti-cholesterol medication, anti-glycemic compound, or an insulin sensitizer.

7. The method of claim 5, wherein the at least one additional compound is vitamin E, vitamin A, vitamin C, a carotenoid, lipoic acid, ubiquinol, ubiquinone, or glutathione.

* * * * *